US012797236B2

(12) United States Patent
Lee et al.

(10) Patent No.: US 12,797,236 B2
(45) Date of Patent: Nov. 17, 2026

(54) OCULAR DRUG DELIVERY DEVICE AND RELATED METHODS

(71) Applicant: Purdue Research Foundation, West Lafayette, IN (US)

(72) Inventors: Chi Hwan Lee, West Lafayette, IN (US); Yannis Mantas Paulus, Ann Arbor, MI (US); Dong Rip Kim, Seoul (KR)

(73) Assignees: Purdue Research Foundation, West Lafayette, IN (US); The Regents of the University of Michigan, Ann Arbor, MI (US); Industry-University Cooperation Foundation Hanyang University, Seoul (KR)

( * ) Notice: Subject to any disclaimer, the term of this patent is extended or adjusted under 35 U.S.C. 154(b) by 257 days.

(21) Appl. No.: 18/699,416

(22) PCT Filed: Oct. 10, 2022

(86) PCT No.: PCT/US2022/046184
§ 371 (c)(1),
(2) Date: Apr. 8, 2024

(87) PCT Pub. No.: WO2023/059933
PCT Pub. Date: Apr. 13, 2023

(65) Prior Publication Data

US 2025/0235350 A1 Jul. 24, 2025

Related U.S. Application Data

(60) Provisional application No. 63/253,686, filed on Oct. 8, 2021.

(51) Int. Cl.
*A61F 9/00* (2006.01)

(52) U.S. Cl.
CPC .... *A61F 9/0017* (2013.01); *A61F 2230/0069* (2013.01); *A61F 2240/001* (2013.01); *A61F 2250/0059* (2013.01); *A61F 2250/0067* (2013.01)

(58) Field of Classification Search
CPC ............ A61F 9/0017; A61F 2230/0069; A61F 2240/001; A61F 2250/0059; A61F 2250/0067
See application file for complete search history.

(56) References Cited

U.S. PATENT DOCUMENTS

| | | | | |
|---|---|---|---|---|
| 6,743,211 | B1 * | 6/2004 | Prausnitz | A61B 5/150083 604/173 |
| 7,918,814 | B2 * | 4/2011 | Prausnitz | A61F 9/0017 604/19 |
| 9,486,362 | B2 * | 11/2016 | Shikamura | A61P 27/02 |
| 2013/0330383 | A1 | 12/2013 | Wirostko | |
| 2020/0138702 | A1 | 5/2020 | Kim et al. | |

FOREIGN PATENT DOCUMENTS

| | | | | |
|---|---|---|---|---|
| KR | 102242800 | | 4/2021 | |
| WO | WO-2015095772 | A2 * | 6/2015 | A61P 27/06 |
| WO | 2017184881 | | 10/2017 | |
| WO | 2020076523 | | 4/2020 | |
| WO | WO-2020252077 | A1 * | 12/2020 | A61M 31/002 |

OTHER PUBLICATIONS

Thakur, et al. "Rapidly dissolving polymeric microneedles for minimally invasive intraocular drug delivery," Drug Deliv. and Transl. Res. (2016) 6:800-815. (Year: 2016).*
International Search Report and Written Opinion dated Feb. 3, 2023 for International Application No. PCT/US2022/046184, 9 pages.

* cited by examiner

*Primary Examiner* — Michael P Cohen
(74) *Attorney, Agent, or Firm* — Hartman Global IP Law; Gary M. Hartman; Domenica N. S. Hartman

(57) ABSTRACT

Ocular drug delivery device and related methods. The ocular drug delivery device includes a contact lens having a curvature configured to fit a cornea of an eye, an array of silicon nanoneedles attached to and protruding from a surface of the contact lens, and a therapeutic drug cargo loaded onto individual nanoneedles of the array of silicon nanoneedles. A method of releasing a therapeutic drug cargo to an eye with the ocular drug delivery device includes applying the ocular drug delivery device to the eye such that the surface of the contact lens contacts the cornea of the eye and individual nanoneedles of the array of nanoneedles are inserted into the cornea. The contact lens dissolves while leaving the individual nanoneedles inserted in the cornea. The individual nanoneedles degrade in the cornea over time causing release of the therapeutic drug cargo loaded thereon.

20 Claims, 20 Drawing Sheets

OCULAR DRUG DELIVERY DEVICE AND RELATED METHODS

CROSS REFERENCE TO RELATED APPLICATIONS

This application claims the benefit of PCT/US2022/46184 filed Oct. 10, 2022, having a priority claim to provisional U.S. patent application No. 63/253,686, filed Oct. 8, 2021. The contents of these prior patent documents are incorporated herein by reference.

STATEMENT REGARDING FEDERALLY SPONSORED RESEARCH OR DEVELOPMENT

This invention was made with government support under CBET 2032529 awarded by the National Science Foundation and under EY033000 awarded by the National Institutes of Health. The government has certain rights in the invention.

BACKGROUND OF THE INVENTION

The present invention generally relates to ocular drug delivery systems, and more particularly to ocular drug delivery devices and related methods.

Many currently common methods of ocular drug delivery rely on topical eye administration using either eye drops or ointments. However, the bioavailability of these methods is limited typically below five percent due to the presence of ocular barriers. Therefore, current therapeutic regimes often require a large dose or frequent topical applications, which burdens patients and increases the risk of side effects such as keratitis, blurred vision, and eye discomfort.

Continued innovation of microneedles has synergistically advanced the field of ocular drug delivery over the past decade, enabling a targeted injection of ocular drugs through the ocular barriers to enhance therapeutic efficacy. However, the clinical implementation of the microneedles in human eyes has been limited due to their relatively large size in a submillimeter range and the exceptional sensitivity of the cornea (i.e., corneal pain). The submillimeter size of the microneedles may also result in corneal damage. Recent efforts have enabled the phenomenal success of producing further miniaturized (e.g., down to 250 μm in base diameter) and biodegradable microneedles for relatively painless ocular drug delivery with reduced side effects. Nevertheless, their long-term therapeutic efficacy remains a challenge due to the rapidly dissolving nature (i.e., burst release) of the biodegradable composites, such as poly (lactic-co-glycolic-acid) (PLGA) and methacrylate hyaluronic acid (MeHA), generally in a range of about 24-120 $\mu m \cdot day^{-1}$. These challenges are particularly problematic in treating chronic ocular diseases, such as corneal neovascularization (CNV), which can benefit from long-term sustained drug delivery.

Vertically ordered arrays of silicon nanoneedles (Si NNs), because of their nanoscale size, low toxicity, and slow biodegradability (e.g., less than 20 $nm \cdot day^{-1}$ in a physiological condition), are of particular interest for minimally invasive and long-term sustained drug delivery. For therapeutic delivery, the surface of silicon nanoneedles can be functionalized to accommodate various drug molecules such as steroids, hormones, proteins, and anticancer agents, and then injected percutaneously or intraperitoneally in humans without significant side effects. Despite great promise, silicon nanoneedles are necessarily bound to a flat, rigid silicon wafer due to the complexity of nanofabrication, which would inevitably result in mechanical mismatch (i.e., discomfort and pain) when interfaced with the curvilinear, soft surface of the cornea. In fact, none of these silicon nanoneedles have been applied to the human eye.

In view of the above, it can be appreciated that there are certain problems, shortcomings or disadvantages associated with the prior art, and that it would be desirable if silicon nanoneedle-based ocular drug delivery devices were available that were capable of at least partly overcoming or avoiding the problems, shortcomings or disadvantages noted above.

BRIEF DESCRIPTION OF THE INVENTION

According to one aspect of the invention, an ocular drug delivery device is provided that includes a contact lens having a curvature configured to fit a cornea of an eye, an array of silicon nanoneedles attached to and protruding from a surface of the contact lens, and a therapeutic drug cargo loaded onto individual nanoneedles of the array of silicon nanoneedles.

According to another aspect of the invention, a method of fabricating the ocular drug delivery device is provided. The method includes forming an array of vertically-ordered, nanoscopic, porous pillars on a substrate, individual pillars of the array of vertically-ordered nanoscopic porous pillars having distal ends extending away from the substrate and proximal ends adjacent the substrate, the individual pillars each having an undercut formed therein at the proximal end thereof that has a minimum diameter of the individual pillar. A flexible film is formed parallel to the substrate with an air gap therebetween. Distal ends of the individual pillars are embedded in the flexible film. The flexible film is peeled away from the substrate such that proximal ends of the individual pillars break away from the substrate at the undercuts thereof and the distal ends of the individual pillars remain embedded in the flexible film, the individual pillars remaining in the flexible film defining the array of nanoneedles. The flexible film is deformed into the contact lens. The individual nanoneedles are loaded with the therapeutic drug cargo.

According to yet another aspect of the invention, a method of releasing a therapeutic drug cargo to an eye. The method includes providing an ocular drug delivery device that includes an array of nanoneedles attached to a surface of a contact lens, applying the ocular drug delivery device to an eye such that the surface of the contact lens contacts the cornea of the eye and individual nanoneedles of the array of nanoneedles are inserted into the cornea, and dissolving the contact lens while leaving the individual nanoneedles inserted in the cornea. The individual nanoneedles degrade in the cornea over time causing release of a therapeutic drug cargo that was loaded onto the individual nanoneedles.

Technical effects of the ocular drug delivery device described above preferably include the ability to provide topical therapeutic treatments therewith such as but not limited to treating various chronic ocular diseases or injuries including glaucoma, cataract, dry eye, and graft rejection. Other aspects and advantages of this invention will be appreciated from the following

BRIEF DESCRIPTION OF THE DRAWINGS

FIG. 2A represents time-lapse schematic illustrations of a biphasic drug delivery process. FIG. 2B represents time-lapse confocal fluorescence microscopy images for the biphasic release of IgG 488 (green) and 647 (red) from the tear-soluble contact lens and the silicon nanoneedles, respectively. FIG. 2C represents time-lapse photographs of an enucleated rabbit eye with the tear-soluble contact lens while being dissolved. FIG. 2D represents time-lapse cross-sectional confocal fluorescence microscopy images of the enucleated rabbit eye with the silicon nanoneedles embedded into the cornea.

FIG. 3A represents a confocal fluorescence microscopy image of the covalently loaded IgG 647 (red) and physically loaded IgG 488 (green) on the surface of the silicon nanoneedles and in the tear-soluble contact lens, respectively. FIG. 3B represents a colored SEM image of a single silicon nanoneedle with a schematic illustration of the drug loading mechanisms. FIG. 3C is a graphical representation of drug dosage loaded on the silicon nanoneedles as a function of surface porosity with the fixed length of 60 μm, with all data represented as mean±standard deviation with n=3 for each group. FIG. 3D is a graphical representation of drug dosage loaded on the silicon nanoneedles as a function of length with the fixed surface porosity of 30%, with all data represented as mean±standard deviation with n=3 for each group. FIG. 3E is a graphical representation of total drug amount when diluted in a 5% v/v solution of ethanol diluent (blue) and standard PBS diluent at the pH of 7.4 (red) as compared to a nondiluted solution (black). with all data represented as mean±standard deviation with n=3 for each group and *p<0.001 compared to the control nondiluted solution using ANOVA. FIG. 3**F represents results of SDS-PAGE revealing the molecular weight of Bev diluted in ethanol diluent (four lanes on the right) as compared to that of a nondiluted solution (2nd lane from the left)

FIG. 4A is a graphical representation of measurement results of the bending stiffness (red lines) and dissolution time (blue lines) of the tear-soluble contact lens when immersed in 5 ml of the simulated tear fluid at 37° C. as a function of the thickness ranging from 4 to 80 μm with molecular weights of 31,000 (triangular symbols) and 61,000 (circular symbols) with all data represented as mean±standard deviation with n=5 for each group. FIG. 4B is a graphical representation of dissolution of the silicon nanoneedles in a 1.4% w/v agarose gel containing a 1 ml of the simulated tear fluid at 37° C. for two months with varied surface porosity ranging from 0-60% and with the presence of a 3 nm-thick pinhole-free $Al_2O_3$ layer, with all data represented as mean±standard deviation with n=5 for each group. FIG. 4C is a graphical representation of cumulative release of IgG 488 and 647 for 120 hours immersed in a 1 ml of the simulated tear fluid at 37° C., each of which was physically and covalently loaded in the tear-soluble contact lens (blue line) and on the surface of the silicon nanoneedles (i.e., porosity=30%) with (red line) and without (purple line) the presence of the $Al_2O_3$ passivation layer, with all data represented as mean±standard deviation with n=3 for each group. FIG. 4D is a graphical representation of results of ELISA to quantify the bioactivity of Bev at 12 and 120 hours of release from the silicon nanoneedles after stored in a refrigerator at 4° C. for one day (red bars) and three days (blue bars), as compared to a new vial of fresh Bev solution as a control (black bars), with all data represented as mean±standard deviation with n=3 for each group, and ***p<0.001 compared to the control nondiluted solution using ANOVA.

FIG. 5A represents time-lapse color, red-free, segmented, and overlay images of CNV on the rabbit eye at day 0 (i.e., pre-therapy) and days 1, 3, 7, 14, and 28 (i.e., on-therapy) using the 10 μm-long (left panel) and 60 μm-long (right panel) silicon nanoneedles. FIG. 5B is a graphical representation of results of VD analysis to quantify the dynamic change of CNV from day 0 to 28, with all data represented as mean±standard deviation with n=3 for each group. FIG. 5C represents time-lapse cross-sectional OCT images of the rabbit eye under therapy using the 60 μm-long silicon nanoneedles at day 0 (i.e., right before and after the lens fitting) and days 1, 7, 14, and 28 (i.e., on-therapy).

FIG. 6A is a graphical representation of in vitro cell viability assay of HCEpiCs that were seeded with (red bars) and without (black bars) the 60 μm-long silicon nanoneedles for three days, with all data represented as mean±standard deviation with n=5 for each group, and *p<0.001 compared to the untreated group using ANOVA. FIG. 6B represents cross-sectional histological view of the rabbit cornea that was stained with both hematoxylin-eosin (H&E) at day 28 on-therapy using the 10 μm-long (top panel) and 60 μm-long (bottom panel) silicon nanoneedles with (left panel) and without (right panel) the presence of Bev. FIG. 6C is a graphical representation of measurement results of the corneal epithelium thicknesses, with all data represented as mean±standard deviation with n=3 for each group, and *p<0.001 among the groups and compared to the untreated group using ANOVA. FIG. 6D represents IHC results of the rabbit limbus that was stained with a p63 cell marker at day 28 on-therapy using the 10 μm-long (top panel) and 60 μm-long (bottom panel) silicon nanoneedles with (left panel) and without (right panel) the presence of Bev. FIG. 6E is a graphical representation of semi-quantification of the p63 cell marker. FIG. 6F is a graphical representation of quantification of endothelial density, with all data represented as mean±standard deviation with n=3 for each group, and ***p>0.005 compared to the untreated group using ANOVA.

DETAILED DESCRIPTION OF THE INVENTION

Figure 1A:
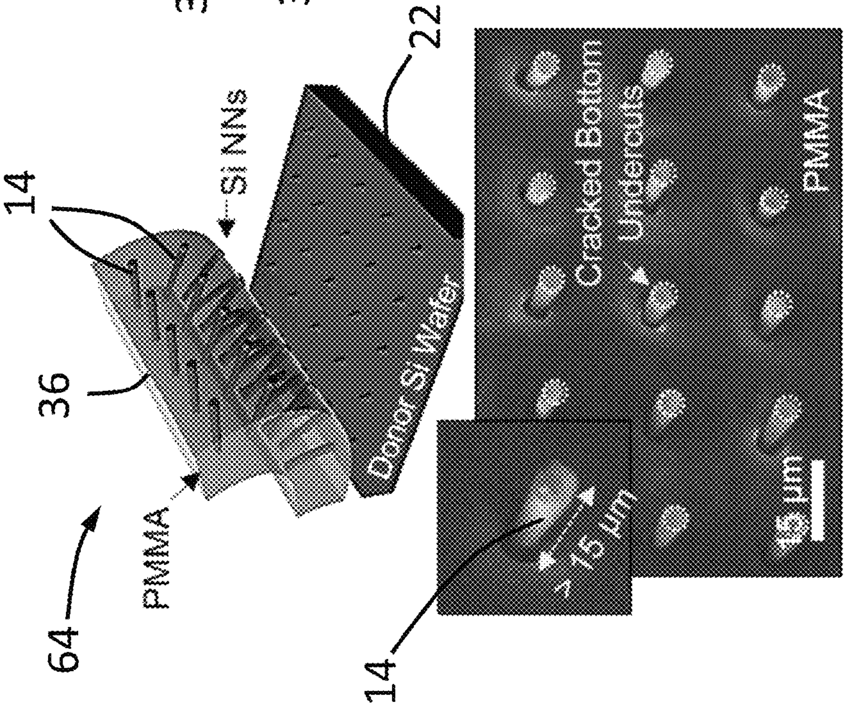
FIGS. 1A through 1D represent a method of producing an ocular drug delivery device in accordance with certain nonlimiting aspects of the invention. The figures include schematic illustrations (top panels) and optical images (bottom panels) for the preparation and physical transfer of as-prepared silicon nanoneedles from a silicon wafer to a tear-soluble contact lens, including (FIG. 1A) transfer of silicon nanoneedles to a PMMA film, (FIG. 1B) deposition of a water-soluble film with an anti-inflammatory drug, (FIG. 1C) hot-pressing of the resulting structure into a lens-shape mold, and (FIG. 1D) loading of therapeutic drugs to the surface of the silicon nanoneedles.

The intended purpose of the following detailed description of the invention and the phraseology and terminology employed therein is to describe what is shown in the drawings, which include the depiction of and/or relate to one or more nonlimiting embodiments of the invention, and to describe certain but not all aspects of what is depicted in the drawings, including the embodiment(s) to which the drawings relate. The following detailed description also describes certain investigations relating to the embodiment(s) depicted in the drawings, and identifies certain but not all alternatives of the embodiment(s) depicted in the drawings. As nonlimiting examples, the invention encompasses additional or alternative embodiments in which one or more features or aspects shown and/or described as part of a particular embodiment could be eliminated, and also encompasses additional or alternative embodiments that combine two or more features or aspects shown and/or described as part of different embodiments. Therefore, the appended claims, and not the detailed description, are intended to particularly point out subject matter regarded to be aspects of the invention, including certain but not necessarily all of the aspects and alternatives described in the detailed description.

To facilitate the description provided below of the embodiment(s) represented in the drawings, relative terms, including but not limited to, "proximal," "distal," "anterior," "posterior," "vertical," "horizontal," "lateral," "front," "rear," "side," "forward," "rearward," "top," "bottom," "upper," "lower," "above," "below," "right," "left," etc., may be used in reference to the orientation of the ocular drug delivery device during its use and/or as represented in the drawings. All such relative terms are useful to describe the illustrated embodiment(s) but should not be otherwise interpreted as limiting the scope of the invention.

As best seen in FIGS. 1D, 2A, 2C, 9B, and 13, an ocular drug delivery device 10 is provided in the form of a contact lens 12 with one or more nanoneedles 14 loaded with a therapeutic drug 16 for delivering the drug via contact with an eye 18. Although it is anticipated that the ocular drug delivery device 10 will most typically be used to release a therapeutic drug cargo to an eye of a human, the ocular drug delivery device 10 may also be used to deliver a drug cargo to the eye of other animals. The contact lens 12 has a curvature configured to fit a cornea 20 of an eye 18. The nanoneedles 14 are configured to contact, penetrate, and embed within the cornea 20 upon application of the contact lens thereto when disposed in an operative position on the eye. Once applied to the eye 18, the contact lens 12 undergoes rapid (e.g., less than one minute) degradation in response to contact with tear fluid leaving the nanoneedles 14 embedded in the cornea 20. The nanoneedles 14 then undergo gradual degradation (e.g., up to one month or more) within the cornea 20 and gradually release therapeutic drug cargos, for example the therapeutic drug 15, linked to the nanoneedles during such degradation. Such drug cargos may include, but are not limited to, various drug molecules such as steroids, hormones, proteins, and anti-cancer agents. Optionally, additional therapeutic drug cargos, such as anti-inflammatory drugs, may be linked to the contact lens 12 and rapidly released upon degradation of the contact lens. The ocular drug device 10 may be used for therapeutic treatments, such as, but not limited to, treating various chronic ocular diseases or injuries including glaucoma, cataract, dry eye, and graft rejection. In some arrangements, the ocular drug delivery device 10 may include a tear-soluble contact lens 12 having nanoneedles 14 on the surface thereof and methods of use thereof suitable for topical of therapeutic drug cargos to an eye. For example, the ocular drug delivery device 10 may provide a flexible, tear-soluble contact lens 12 having a vertically ordered array of biodegradable silicon nanoscopic needles (nanoneedles) 14 on and projecting radially outwardly from the concave surface of the contact lens 12.

Figure 7A:
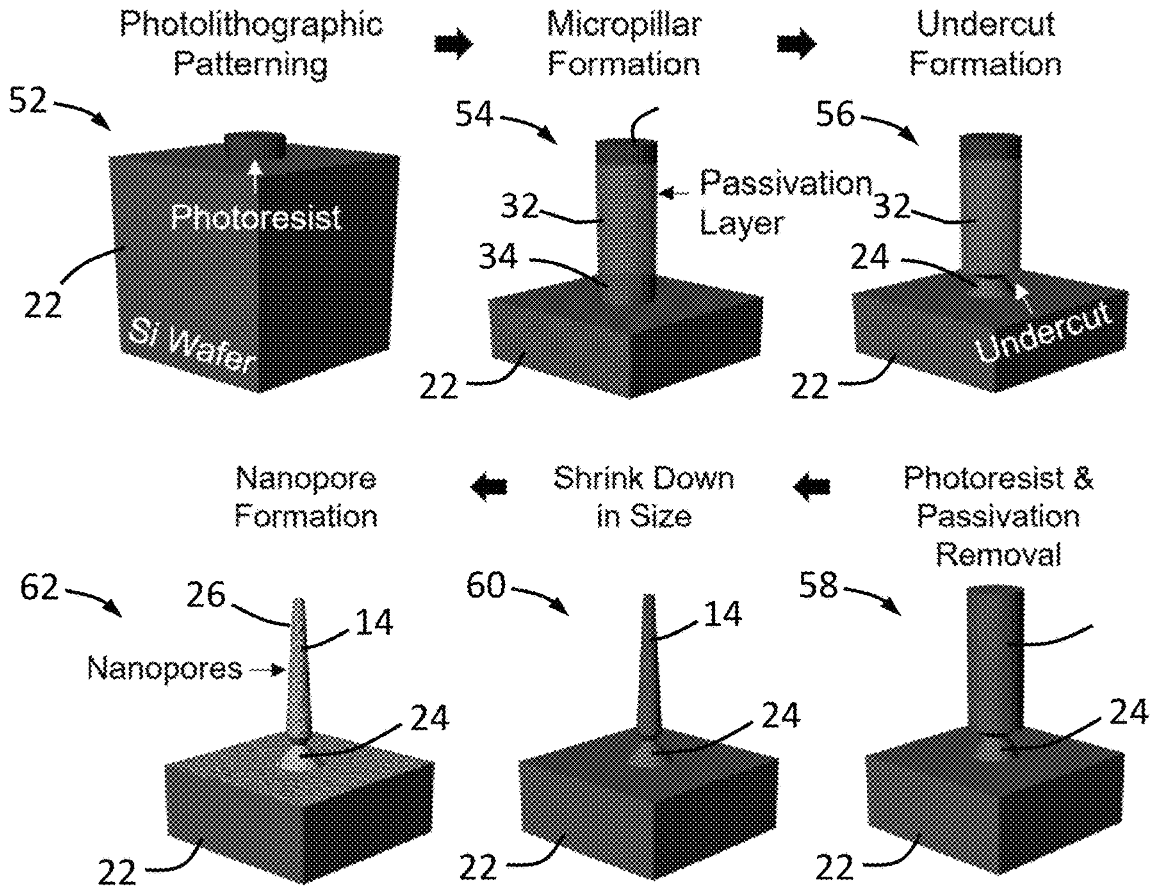
FIG. 7A is a schematic illustration describing the fabrication of the silicon nanoneedles on a silicon wafer.
Figure 7B:
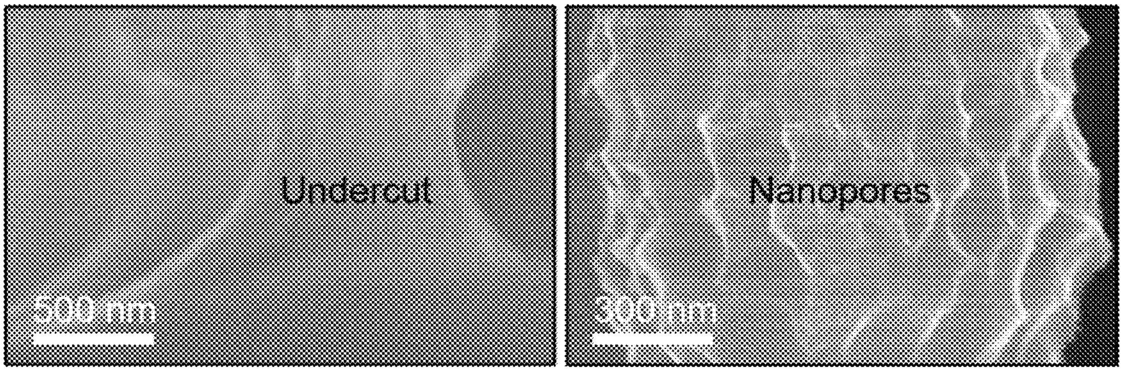
FIG. 7B represents SEM images highlighting the undercut and nanopores on the bottom root and along the surface of the silicon nanoneedles, respectively.
Figure 8A:
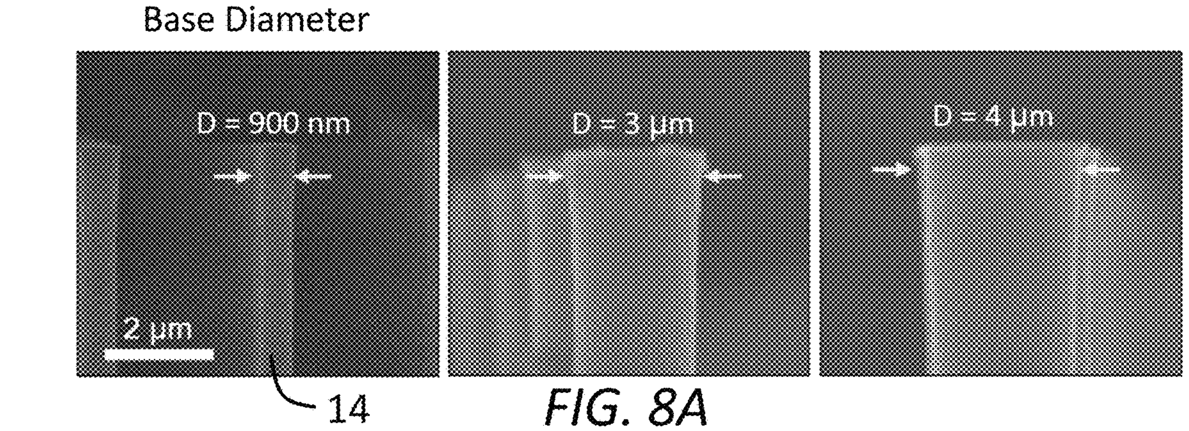
FIGS. 8A through 8D represent SEM images of the silicon nanoneedles with varied geometric configurations in terms of the (FIG. 8A) base diameter (i.e., >900 nm), (FIG. 8B) aspect ratio (i.e., 6-38), (FIG. 8C) tip morphology (i.e., cylindrical, conical, or tapered end), and (FIG. 8D) surface porosity (i.e., 0-60%).
Figure 8B:
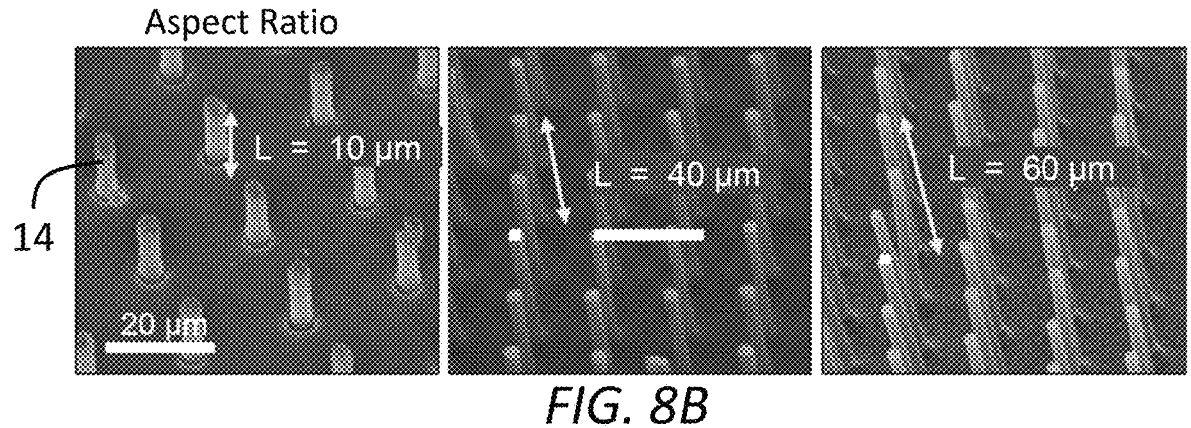
Figure 8C:
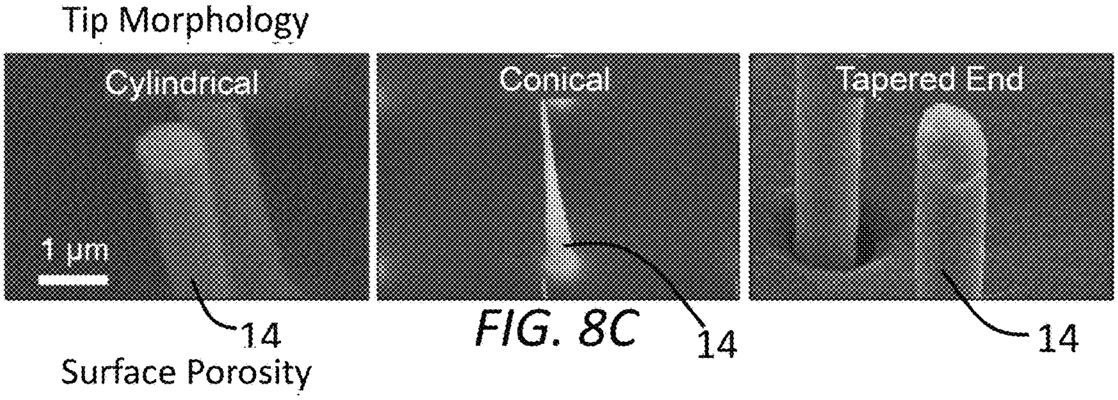
Figure 8D:
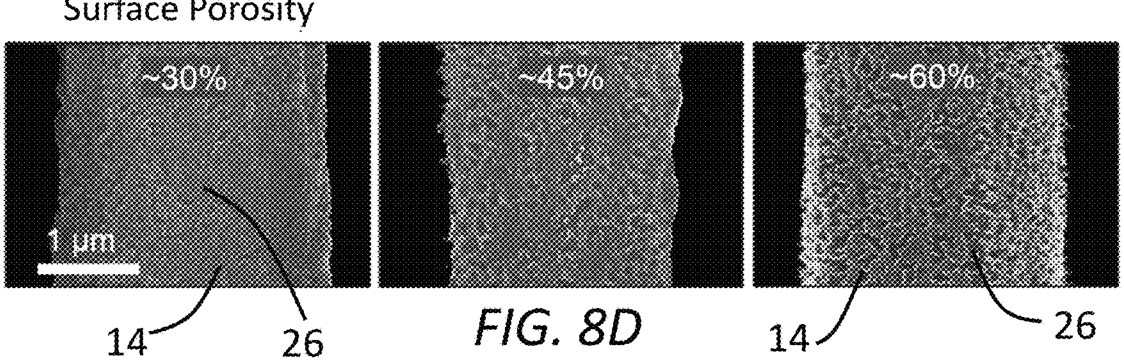

FIGS. 1A through 1D and 7A represents aspects of a nonlimiting method 50 that may be used to fabricate the silicon nanoneedles 14 on a silicon wafer 22 using a photolithographic patterning process, followed by a series of dry and wet etching processes to form undercuts 24 and pores 26 at bottom roots and along surfaces, respectively as best seen in FIG. 7B. As seen in FIG. 7A, and with reference to FIGS. 1A and 1B, a bulk silicon wafer 22 (e.g., p-type; 525 μm-thick; 0-100 Ω·cm) may be immersed in a buffered oxide etchant (e.g., for one minute) to remove a native oxide layer thereon. At step 52 photolithographic patterning and anisotropic deep reactive ion etching (DRIE) may be performed to define a vertically ordered array of silicon micropillars 30 with a predetermined aspect ratio. At step 54, a thin passivation layer 32, such as $(C_xF_y)$ n polymer, may be coated on the surface of the silicon micropillars 30 using octafluorocyclobutane ($C_4F_8$) gas (e.g., flow rate of 130 sccm under a radio frequency (RF) plasma power of 800 W). Bottom roots 34 of the silicon micropillars 30 may be intentionally unpassivated using an anisotropic dry etching process to form the undercuts 24 at step 56, for example, using sulfur hexafluoride ($SF_6$) gas (e.g., flow rate of 85 sccm under RF plasma power and platen power of 450 W and 14 W, respectively). At step 58 A remaining passivation layer on the surface of the silicon micropillars 30 may be removed, for example, using an oxygen ($O_2$) plasma (e.g., 20 sccm; 150 W; 50 mTorr; for 15 minutes) and piranha cleaning in a mixture solution containing, for example, a 75% of sulfuric acid ($H_2SO_4$) and a 25% of hydrogen peroxide ($H_2O_2$) by volume. At step 60, the overall size of the silicon micropillars of the resulting silicon micropillars 30 are shrunk from microscale to nanoscale to form the silicon nanoneedles 14, for example by being immersed in a phosphate-buffered saline (PBS; pH=7.4; 67° C.; eight hours or more) and then in potassium hydroxide (KOH; 15% wt; 25° C.; ten minutes).

At step 62, the nanopores 26 are formed in and along the surfaces of the silicon nanoneedles 14. For example, a metal-assisted chemical etching (MACE) process may be performed in which the silicon nanoneedles 14 are immersed in a mixture solution containing silver nitrate ($AgNO_3$; 20 mM) and hydrofluoric acid (HF; 49%) solution to form the nanopores 26 along the surface of the silicon nanoneedles 14. For example, overall surface porosity of the silicon nanoneedles 14 may be controllably increased to about thirty, forty-five, or sixty percent by performing the MACE process for about thirty, sixty, or ninety seconds, respectively. The silicon nanoneedles 14 may then be immersed in a silver etchant solution (TFS, KI-I2 complex liquid) for about one minute to remove the remaining silver residues on surfaces of the silicon nanoneedles 14. A relatively thin (e.g., 3 nm-thick) pinhole-free passivation layer comprising, for example, $Al_2O_3$ may be deposited using atomic layer deposition (ALD; trimethylaluminum precursor; pulse of 0.015 s; 0.2 Torr; nitrogen ($N_2$) purge at 20 sccm for 20 s; substrate temperature at 150° C.). In such embodiments, the ALD process may be repeated as necessary to obtain a desired layer thickness (e.g., about 1 Å-thick $Al_2O_3$ layer per cycle; repeated thirty times for total thickness of 3 nm).

Parameters of the photolithographic patterning process, the dry etching process, and the wet etching process may be adjusted to control the geometric configuration of the silicon nanoneedles 14, for example, in terms of the base diameter (i.e., >900 nm), aspect ratio (i.e., 2-67), tip morphology (i.e., cylindrical, conical, or tapered end), and surface porosity (i.e., 0-60%). Nonlimiting examples of possible configurations are represented in FIGS. 8A through 8D.

Figure 1B:
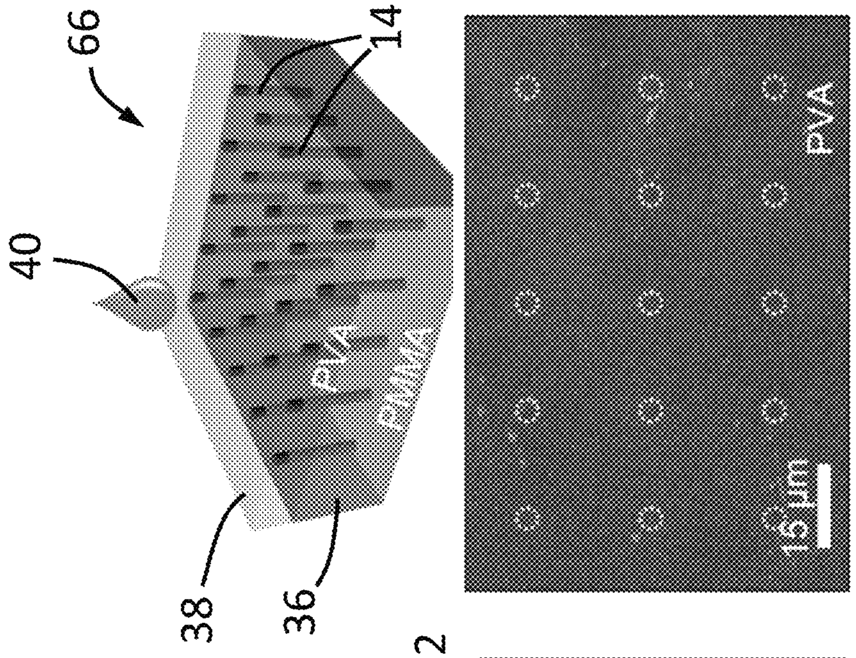

FIGS. 1A and 1B provide schematic illustrations (top panels) and optical images (bottom panels) for aspects of a nonlimiting method for transferring the as-prepared silicon nanoneedles 14 at step 62 from the donor silicon wafer 22 to a tear-soluble contact lens. First, a thin layer 36 (e.g., about 200 μm-thick) of polymethyl methacrylate (PMMA) may be deposited (e.g., spin-cast) as a coating over the silicon nanoneedles 14 and annealed (e.g., 80° C. for two hours). An air gap (e.g., about 16 μm) may be formed at the bottom root of the silicon nanoneedles due to surface tension. At step 64, a mechanical peeling process at a constant rate (e.g., 50 mm·min$^{-1}$) is then performed using an automated peeling apparatus (FIG. 1A, top panel). During this peeling process, mechanical stresses intensively concentrate at the bottom undercuts 24 of the silicon nanoneedles 14 to generate cracks, leading to their physical separation from the donor silicon wafer 22. A scanning electron microscopy (SEM) image (FIG. 1A, bottom panel) shows nonlimiting examples of the bottom undercuts of silicon nanoneedles separated with the peeling process. The silicon nanoneedles are uniformly cracked with an exposed length of about 15 μm from the layer 36 of PMMA.

At step 66, a water-soluble PVA solution diluted in distilled water (e.g., 2% wt; molecular weight=31,000) may be deposited (e.g., spin-cast) across the exposed surface of the exposed bottom undercuts 24, followed by a thermal annealing process (e.g., 60° C. for one hour) to polymerize the PVA solution to form a PVA film 38 (e.g., about 40 μm-thick) with the bottom undercuts 24 of the silicon nanoneedles 14 embedded therein. An SEM image (FIG. 1B, bottom panel) shows an example of the polymerized PVA film 38 covering the ends of the silicon nanoneedles 14 at the undercuts 24. For enhanced therapeutic efficacy, the PVA film 38 may be mixed with anti-inflammatory drug 40 and/or other type of ocular drug to enable a biphasic drug release, that is, initial quick release of an anti-inflammatory drug 40 from the tear-soluble contact lens 12 followed by a long-term sustained release of a therapeutic ocular drug 16 from the silicon nanoneedles 14.

Figure 1C:
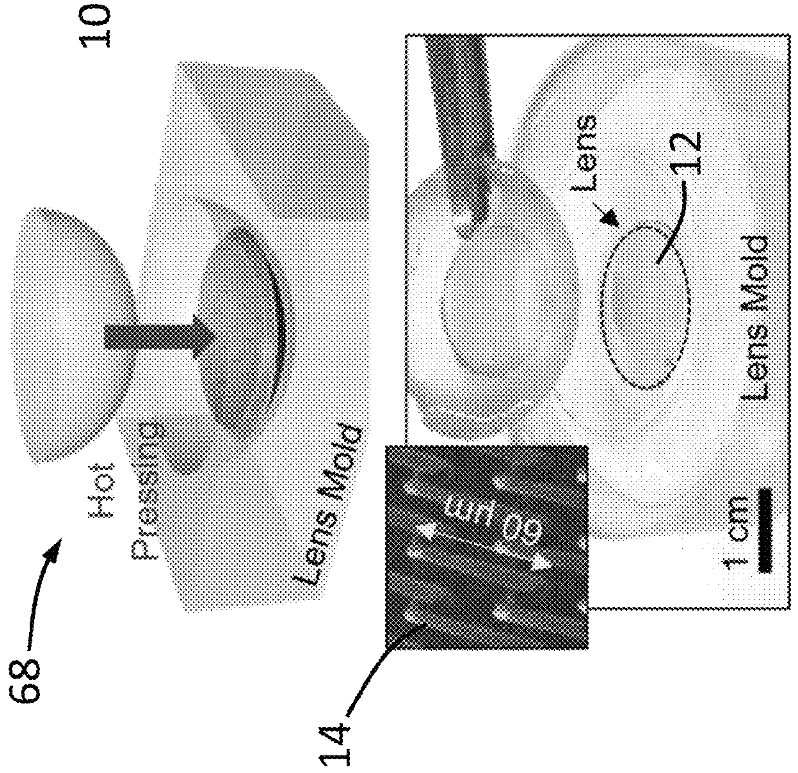

At step 68, the entire structure (i.e., PMMA/silicon nanoneedles/PVA) may be trimmed into a circular shape (e.g., 10-15 mm in diameter), and 4 the trimmed structure may then be pressed into a contact lens-shaped mold (e.g., 90° C. for five minutes; FIG. 1C) with the PMMA layer 36 facing toward the concave side (upwards as depicted in the drawing) of the resulting contact lens structure 12. The contact lens 12 is preferably configured to fit a cornea of an eye, and may have various base curve radii ranging, for example, from 8.3 to 9.0 mm. For example, contact lens-shaped molds for artificial eyes having different base curve radii ranging from 8.3 to 9.0 mm may be used. The PMMA layer 36 may then be selectively removed with, for example, acetone (e.g., immersion at 70° C. for four hours). An SEM image (FIG. 1C, bottom panel, inset) shows exemplary exposed silicon nanoneedles 14 from the surface of a PVA contact lens 12 with an exposed length of about 60 μm. The length of the silicon nanoneedles 14 is preferably within a maximum injectable depth (e.g., about 43-63 μm) corresponding to the human corneal epithelial layer (e.g., about 50 μm-thick) to avoid or reduce the likelihood of causing irreversible corneal stromal scarring.

Figure 1D:
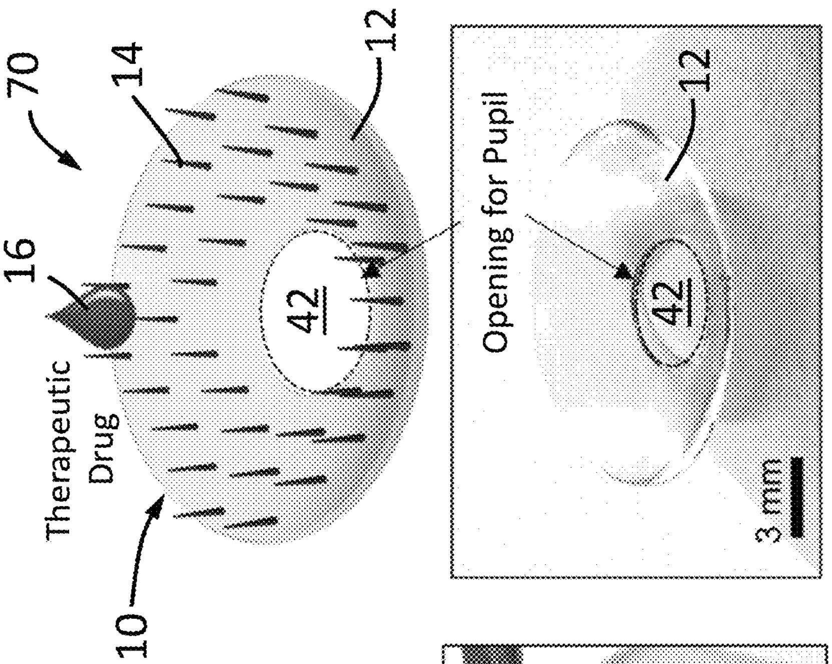
Figure 9A:
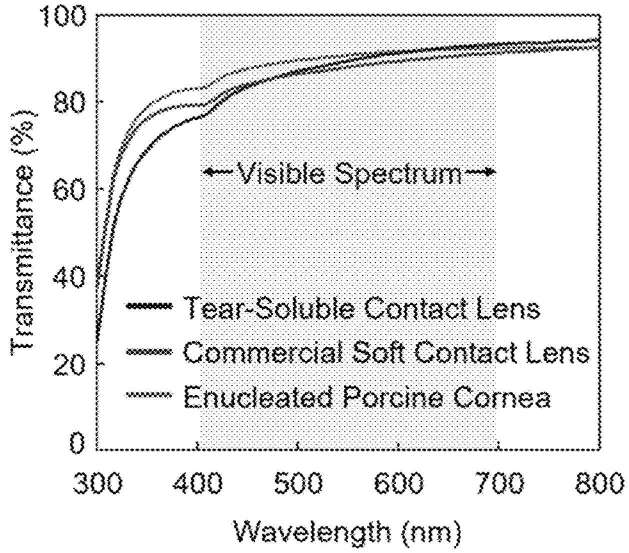
FIG. 9A is a graphical representation of transmittance of the silicon nanoneedles on a tear-soluble contact lens as compared to a commercial soft transparent contact lens as well as an enucleated porcine cornea.
Figure 9B:
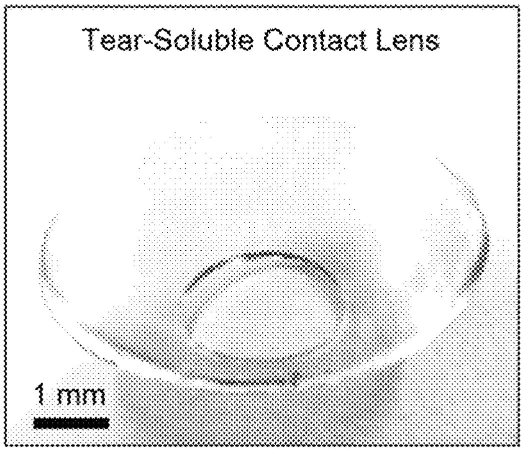
FIGS. 9B through 9D represent photographs of the silicon nanoneedles on a tear-soluble contact lens (FIG. 9B), commercial soft transparent contact lens (FIG. 9C), and enucleated porcine cornea (FIG. 9D), respectively.
Figure 9C:
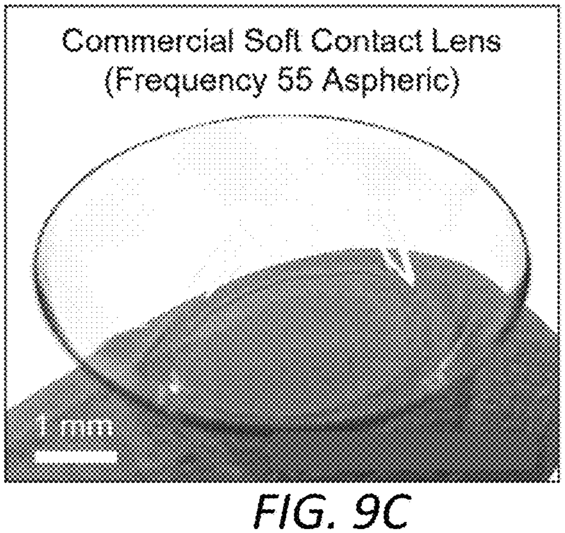
Figure 9D:
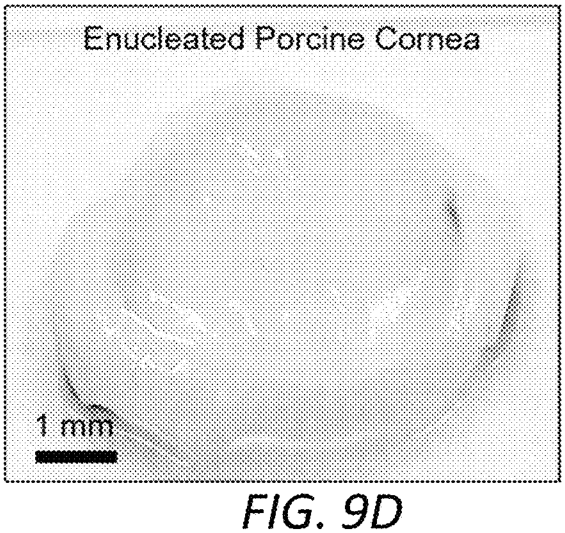

At step 70, the antibody therapeutic ocular drug 16 is applied to the nanoneedles 14. The surface of the silicon nanoneedles 14 may be chemically functionalized with silane to form a strong covalent cross-linker bond to the therapeutic ocular drug 16, such as an antibody therapeutic ocular drug, of interest (FIG. 1D, top panel). A hole 42 (e.g., about 2-8 mm in diameter) may be punched at the pupil area of the tear-soluble contact lens (FIG. 1D, bottom panel) to promote clear vision at the central visual axis of the eye while minimizing a potential risk of corneal stromal haze when operatively disposed on an eye. The thickness of the tear-soluble contact lens 12 may be in a range of about 37-43 μm, which is thinner than standard commercial contact lenses (e.g., about 50-180 μm-thick). Preferably, the tear-soluble contact lens 12 may provide visual transparency prior to its dissolution in tear fluid such that the optical transmission is comparable to that of a commercial soft contact lens as well as an enucleated porcine cornea in the visible spectrum (i.e., 400-700 nm) (FIG. 9A).

Figure 2A:
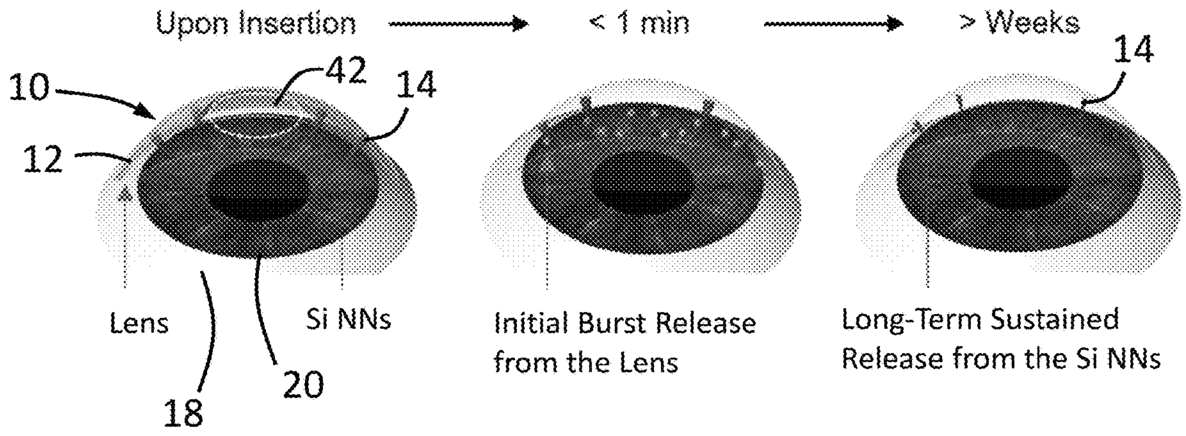
FIGS. 2A through 2D represent working principles and a nonlimiting control strategy for the ocular drug delivery device produced with the method of FIGS. 1A through 1D.

FIG. 2A schematically represents the working principle of the silicon nanoneedles 14 in ocular drug delivery using the ocular drug delivery device 10. Specifically, the silicon nanoneedles 14 are embedded within the corneal epithelial layer by gently inserting the tear-soluble contact lens 12 onto the eye (FIG. 2A, left). The tear-soluble contact lens 12 is then completely dissolved in tear fluid, preferably within less than a minute, through which an initial burst release of the anti-inflammatory 40 or other ocular drugs may optionally be carried out (FIG. 2A, middle). In parallel, the embedded silicon nanoneedles 14 are gradually dissolved in the cornea 20 over a long period of time (e.g., over a month)

via a hydrolysis reaction of the silicon nanoneedles 14 into silicic acid and hydrogen in the presence of tear fluid, through which a long-term sustained release of the therapeutic drug(s) 16 is carried out (FIG. 2A, right).

As used herein, the term "nanoneedle" refers to a nanoscale or nanoscopic needle that is generally conical or tubular in shape and has geometric features that include minimum tip diameters of less than 1 μm, base diameters of less than 10 μm, and lengths of at least 1 μm. silicon nanoneedles disclosed herein preferably have minimum tip diameters of about 50 to 900 nm, base diameters of about 0.9 to 5 μm, and lengths of about 1 to 100 μm, and more preferably minimum tip diameters of about 150 nm, base diameters of about 2 to 4 μm, and lengths of about 10 to 70 μm.

The porosity of the silicon nanoneedles 14 relates to the loading capacity and release rate of their drug cargos. The porosity of the silicon nanoneedles 14 may range from about 0 to about 80 percent, for example, from about 0 to 60 percent. In certain embodiments, the silicon nanoneedles 14 preferably have an average porosity of about 15 to 60 percent, more preferably between about 25 to 50 percent, for example, about 45 percent. In certain embodiments, the ocular drug delivery device 10 may have a drug loading capacity of 10 μg or more per 1×1 cm2 area of the surface of the film to which the silicon nanoneedles are attached, as a nonlimiting example, 15 μg to about 50 μg, per 1×1 $cm^2$.

The silicon nanoneedles 14 may have a drug release profile that includes a rapid release of their drug cargos within 24 hours post-inoculation until they gradually reach a sustained, predetermined dose that is released and maintained for a period of time. In such embodiments, 24 hours or less after the inoculation, the silicon nanoneedles 14 preferably provide a sustained release dose sufficient to provide a therapeutic effect for the application (e.g., at or above a minimum inhibitory concentration for the drug of interest), and more preferably provide a sustained release dose above a half maximal inhibitory concentration ($IC_{50}$) value for the application. Such sustained releases at the predetermined doses (e.g., after the initial rapid release) preferably last for a period of time of at least 24 hours, for example, up to about 28 days or more. Such sustained release doses and time periods may be controlled based on the specific application.

Nonlimiting embodiments of the invention will now be described in reference to experimental investigations leading up to the invention. Specifically, comprehensive studies in vitro, ex vivo, and in vivo were conducted not only to reveal the underlying properties of the ocular drug delivery device but also to validate therapeutic efficacy and biosafety in a rabbit CNV model as compared to the current gold standard therapy.

For these investigations, an ocular drug delivery device 10 having a contact lens 12 with a vertically ordered array of biodegradable silicon nanoneedles 14 thereon was produced in accordance with the above-described processes. The surfaces of the silicon nanoneedles 14 were treated with 3-triethoxysilylpropyl succinic anhydride (TESPSA) to form an amide type of covalent bonding to antibody ocular drugs 16, such as an anti-vascular endothelial growth factor antibody bevacizumab (Bev). Specifically, IgG labeled with Alexa Fluor 647 and 488 were used to model covalently bonded Bev along the surface of the silicon nanoneedles 14 and physically loaded burst release drugs (e.g., anti-inflammation drugs 40) in the tear-soluble contact lens 12, respectively. For the covalent bonding of IgG 647, a 500 μl of TESPSA was applied to the silicon nanoneedles 14 at room temperature for ten minutes to functionalize the surface with silane and then washed with anhydrous ethanol. More specifically, a 30 μg of IgG 647 was prepared by mixing a 50 μl of IgG 647 with a concentration of 600 $\mu g \cdot ml^{-1}$ and a 950 μl of anhydrous ethanol. In this solution, the silicon nanoneedles 14 were immersed for thirty minutes at room temperature, followed by rinsing with anhydrous ethanol. The covalent bonding process for Bev was identical to that for the IgG 647. For the physical loading of IgG 488, a 10 μl of IgG 488 with a concentration of 100 $\mu g \cdot ml^{-1}$ was mixed with a 1.5 ml of PVA (2% wt; Molecular Weight=31,000) and stirred at 300 rpm for one minute.

Figure 2B:
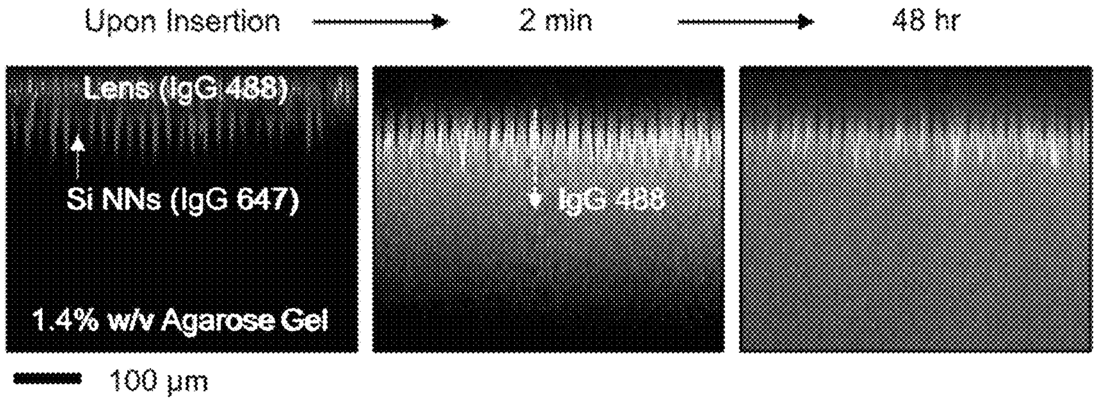

FIG. 2B represents a series of confocal fluorescence microscopy images that demonstrate exemplary biphasic releases of immunoglobulins (IgG) labeled with Alexa Fluor 488 (green) and 647 (red) from the tear-soluble contact lens 12 and the silicon nanoneedles 14, respectively. A 1.4% w/v agarose gel containing a 1 ml of simulated tear fluid was used to mimic the human cornea in the mechanical stiffness (E≈20 kPa) and tear contents (>80%). The simulated tear fluid used to obtain this exemplary data included 100 ml of deionized water mixed with a 0.68 g of sodium chloride (NaCl), a 0.22 g of sodium bicarbonate ($NaHCO_3$), a 0.008 g of calcium chloride dihydrate ($CaCl_2 \cdot 2H_2O$), and a 0.14 g of potassium chloride (KCl). The results showed that the initial burst release of the IgG 488 (green) occurred within the first minute from the dissolution of the tear-soluble contact lens 12 while the release of the IgG 647 (red) barely appeared over forty-eight hours.

Figure 2C:
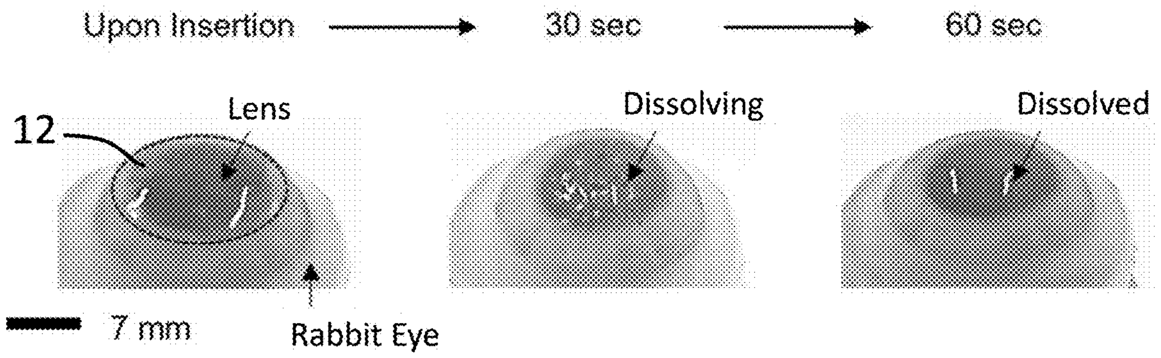
Figure 2D:
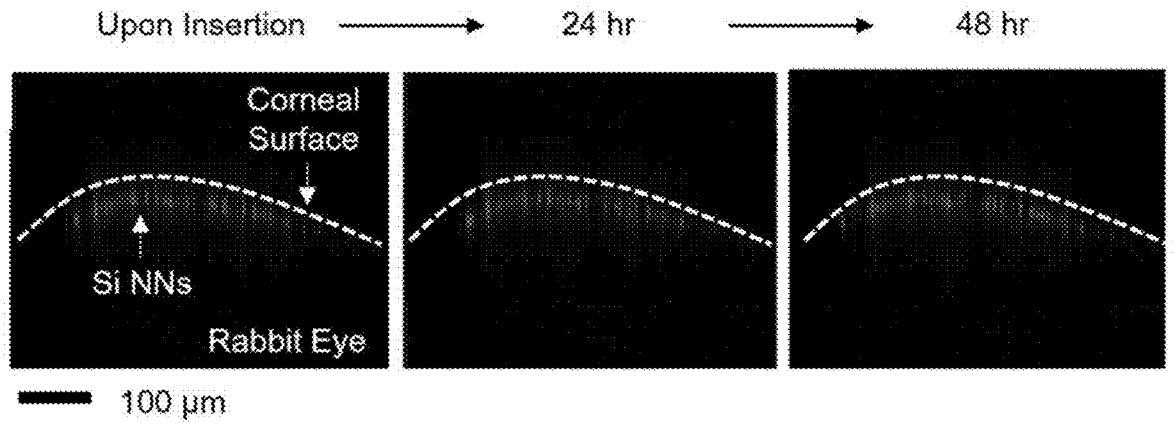
Figure 10:
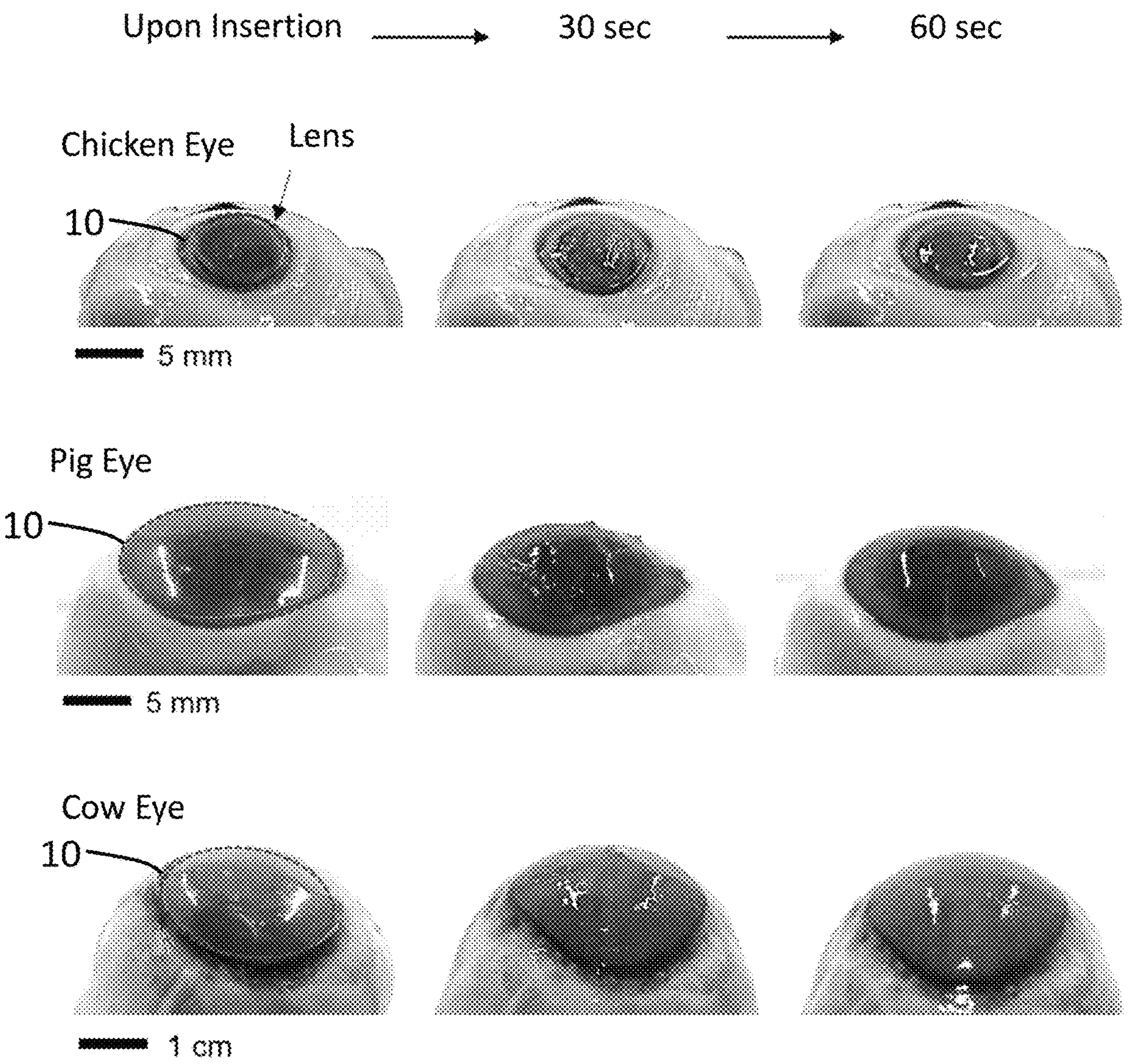
FIG. 10 represents time-lapse photographs of the tear-soluble contact lens with a tailored size to fit a variety of corneal shapes including a chicken eye (top panel), a pig eye (middle panel), and a cow eye (bottom panel).

FIG. 2C presents the corresponding ex vivo results with an enucleated rabbit eye that provides anatomical similarity to the human eye in the corneal thickness (540-560 μm) and curvature (8.3-9.0 mm in base curve radius). The tear-soluble contact lens was inserted onto the rabbit eye and then completely dissolved within a minute in the presence of the simulated tear fluid. As shown in FIG. 10, the overall size of the tear-soluble contact lens was adjustable to fit a variety of corneal shapes including the chicken eye (10 mm in diameter; 5.2 mm in base curve radius), pig eye (14 mm in diameter; 9 mm in base curve radius), and cow eye (30 mm in diameter; 15 mm in base curve radius). The silicon nanoneedles 14 were invisible across the corneal surface owing to the nanoscale size effect, thereby inducing no noticeable corneal punctures. The confocal fluorescence microscopy shown in FIG. 2D confirms that the entire length (i.e., 60 μm-long) of the silicon nanoneedles 14 was embedded into the cornea without being washed away over time in the presence of the simulated tear fluid. The results also confirm that most of the IgG 647 (red) remained at the surface of the silicon nanoneedles 14 over 48 hours, implying that the pre-corneal drug residence time was substantially prolonged as compared to topical eye drops (i.e., 1-30 minutes) and ointments (i.e., 1-8 hours).

Figure 3B:
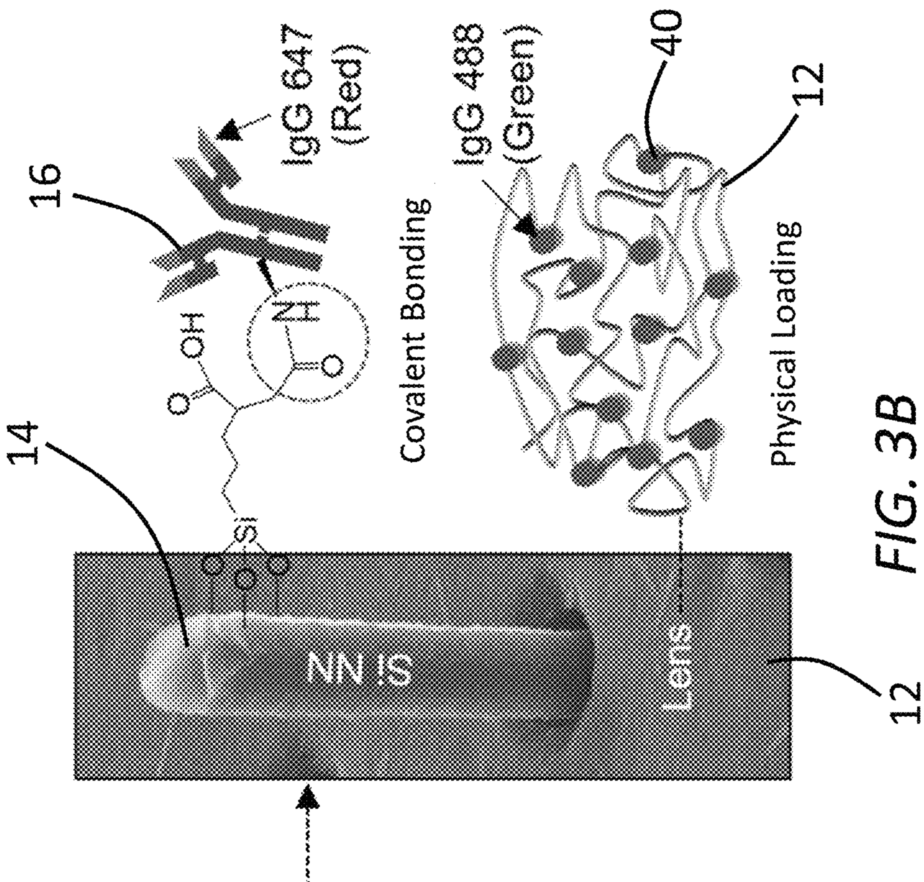
FIGS. 3A through 3F represent a drug loading mechanism and controls.
Figure 3A:
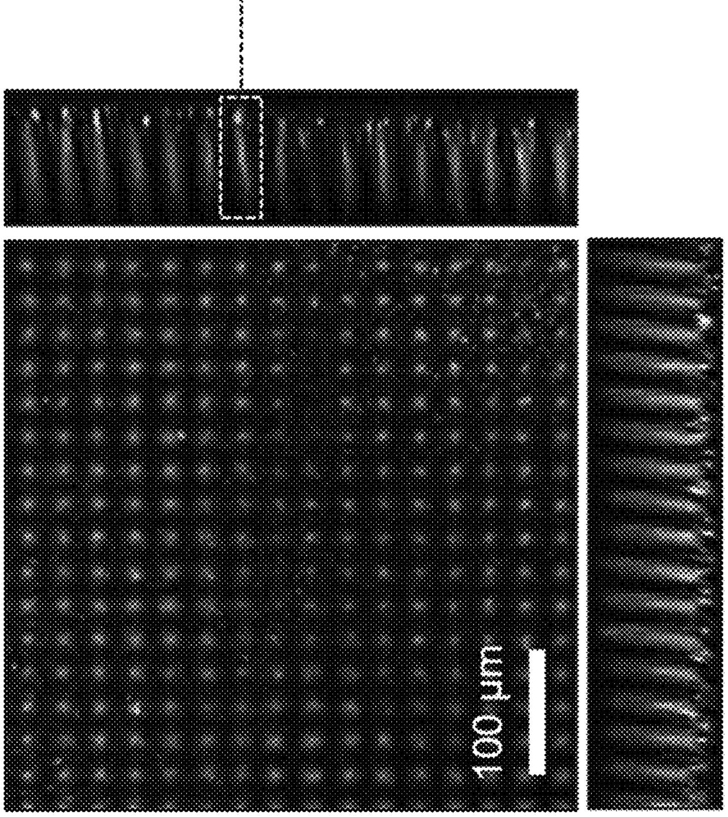
Figure 3C:
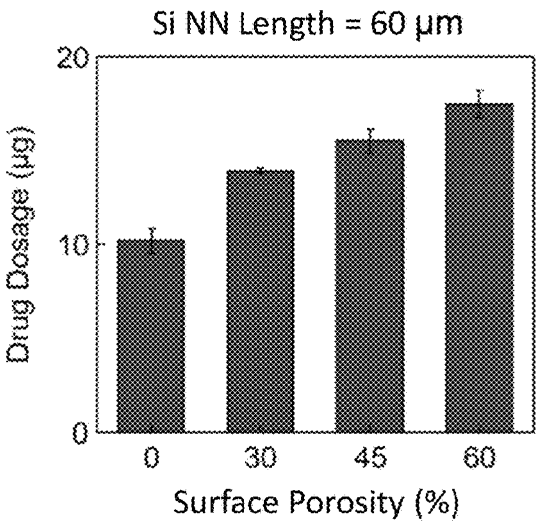
Figure 3D:
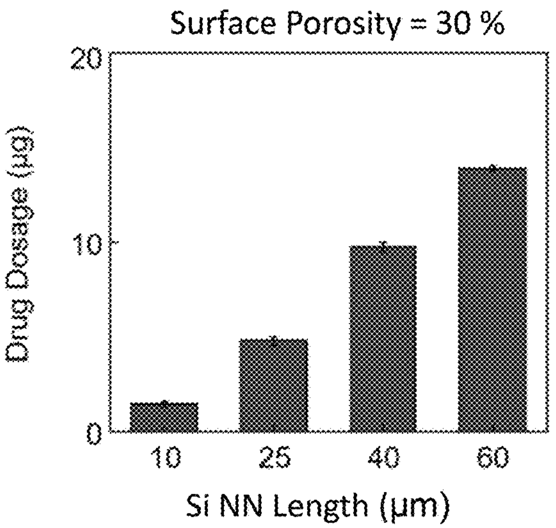
Figure 13:
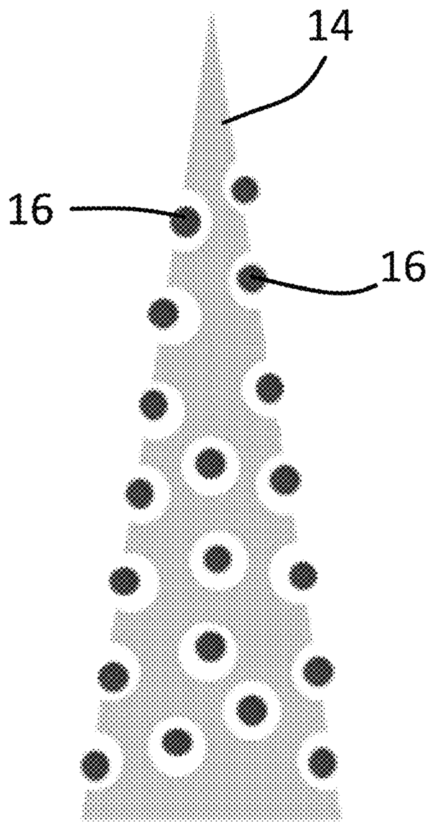
FIG. 13 is diagrammatic representation of a silicon nanoneedle (Si NN) with drug molecules bonded thereto according to nonlimiting aspects of the present invention.

FIG. 3A provides a representative confocal fluorescence microscopy image showing that the IgG 647 (red) was uniformly loaded across the surface of the silicon nanoneedles 14 via covalent bonding. The IgG 488 (green) was physically encapsulated (i.e., physical loading) in the tear-soluble contact lens 12 with negligible residues of the IgG 647 (red). FIG. 3B provides a colored SEM image of a single silicon nanoneedle 14 along with a schematic illustration of the drug loading mechanisms. The drug dosage was controlled through the modulation of either the surface porosity caused by the nanopores 26 or size of the silicon nanoneedles 14. For instance, the dosage of the IgG 647 increased from 10.17±0.70 to 17.44±0.74 μg as the surface porosity of the silicon nanoneedles increased from 0 to 60% at a fixed length of 60 μm (FIG. 3C). Likewise, the dosage increased from 1.41±0.16 to 13.88±0.14 μg as the length of the silicon nanoneedles increased from 10 to 60 μm at a fixed surface porosity of 30% (FIG. 3D). With reference to FIG. 13, the drug molecules, for example any of various ocular drug molecules, bond to the silicon nanoneedle(s) 14 covalently and/or physically. As already described, the drug molecules are attached through covalent bonding to the surface of the nanoneedle 14. In addition, because the surface of silicon nanoneedles have nanoscale pores (nanopores 26), the drug molecules may also be physically bonded to the nanoneedle by being physically trapped inside the nanopores 26. In the present examples, the pore density (porosity) of the nanopores 26 on the surfaces of the silicon nanoneedles may be adjusted and selected to precisely control drug dosage. For example, more nanopores 26 will typically have more drug molecules physically trapped inside the nanopores. However, the ocular drug delivery device 10 of the present invention would also still operable without the presence of the nanopores 26, although such a configuration may reduce the ability to control drug dosage as effectively.

Figure 3E:
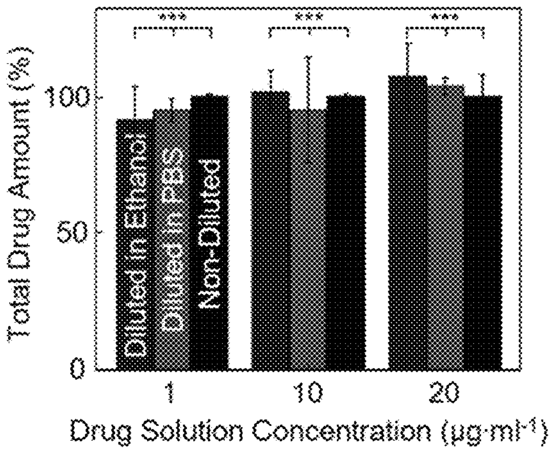
Figure 3F:
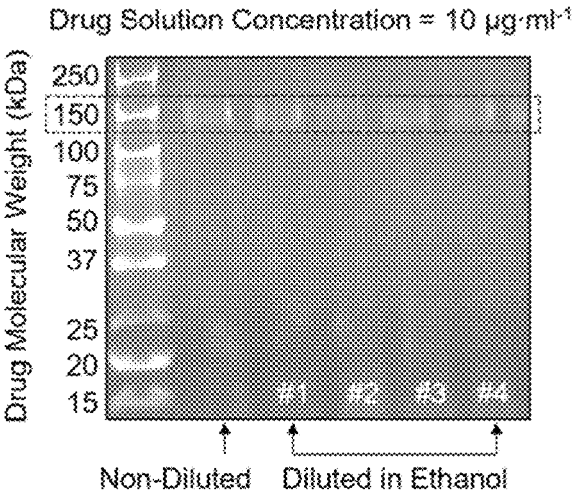

The drug solution (e.g., Bev) was diluted into a range of 1-20 $\mu g \cdot ml^{-1}$ using an anhydrous (i.e., greater than or equal to 99.9%) ethanol diluent to avoid any dissolution of the tear-soluble contact lens during the loading process. FIG. 3E presents that there was no significant difference in the total amount of Bev when diluted in a 5% v/v solution of ethanol diluent (blue bars) and standard phosphate-buffered saline (PBS) diluent at a pH of 7.4 (red bars) as compared to a nondiluted drug solution (black bars), according to the one-way analysis of variance (ANOVA) results with *p<0.001 (n=5 for each group). In addition, the results of sodium dodecyl sulfate polyacrylamide gel electrophoresis (SDS-PAGE) in FIG. 3**F show that the molecular weight of Bev diluted in ethanol diluent (four lanes on the right) was comparable to that of a nondiluted drug solution (2nd lane from the left) with a clear band at 150 kDa. In turn, there was no significant impact of ethanol diluent on the in vitro stability of Bev.

Figure 4A:
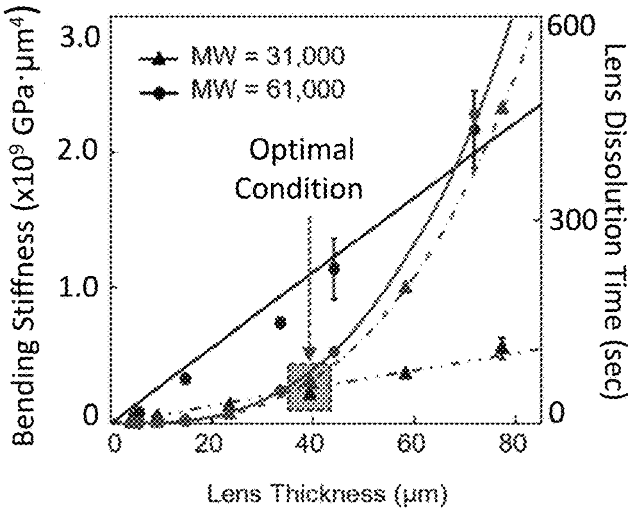
FIGS. 4A through 4D represent dissolution kinetics and drug release kinetics.

The intrinsic properties of the tear-soluble contact lens 12 in terms of bending stiffness (i.e., flexural rigidity) and dissolution rate were controlled to promote both easy handling during lens fitting and rapid dissolution in tear fluid thereafter. FIG. 4A presents the bending stiffness (red lines) and dissolution time (blue lines) of the tear-soluble contact lens when immersed in 5 ml of the simulated tear fluid at 37° C. as a function of the lens thickness ranging from 4 to 80 μm. For comparison, two different molecular weights of the tear-soluble contact lens 12, i.e., 31,000 (triangular symbols) and 61,000 (circular symbols), were tested. The results show that the bending stiffness of the tear-soluble contact lens decreased to cubic of the lens thickness, while the dissolution rate decreased by more than 4-fold (i.e., from 5.7 to 1.3 $\mu m \cdot sec^{-1}$) as the molecular weight increased from 31,000 to 61,000. The green highlighted area in the graph indicates the empirically identified optimal condition using a 40 μm-thick tear-soluble contact lens 12 with the molecular weight of 31,000 at which both the bending stiffness (i.e., greater than $3.07 \times 10^8$ $GPa \cdot \mu m^4$) and dissolution rate (i.e., 5.7 $\mu m \cdot sec^{-1}$) were sufficiently large to not only resist against bending, folding, and twisting but also to allow for dissolving within a minute in the presence of the simulated tear fluid.

Figure 4B:
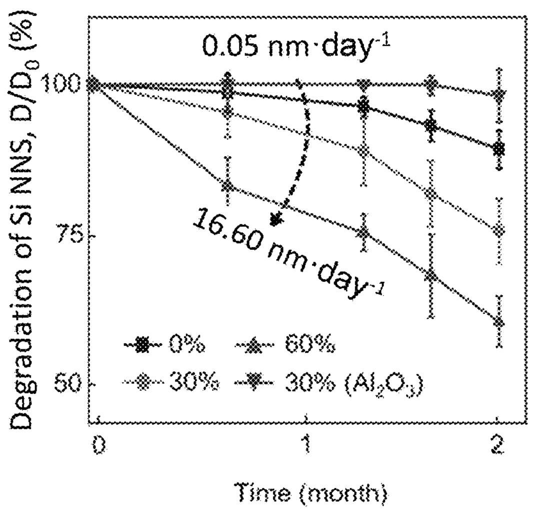
Figure 11:
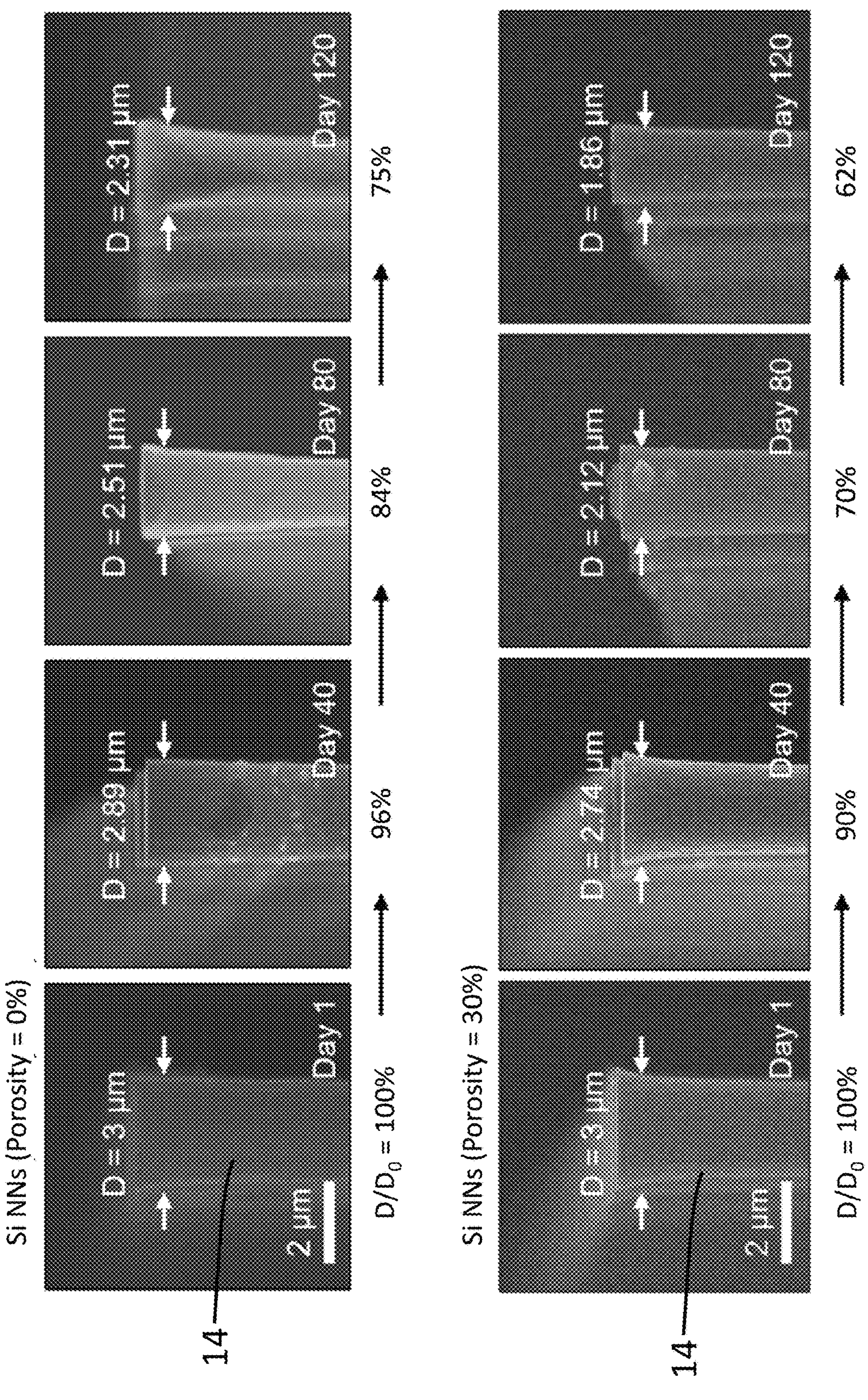
FIG. 11 represents time-lapse SEM images of the silicon nanoneedles while being degraded at days 1, 40, 80, and 120 with varied surface porosity ranging from 0 to 60% and with the presence of a 3 nm-thick pinhole-free $Al_2O_3$ layer.
Figure 11:
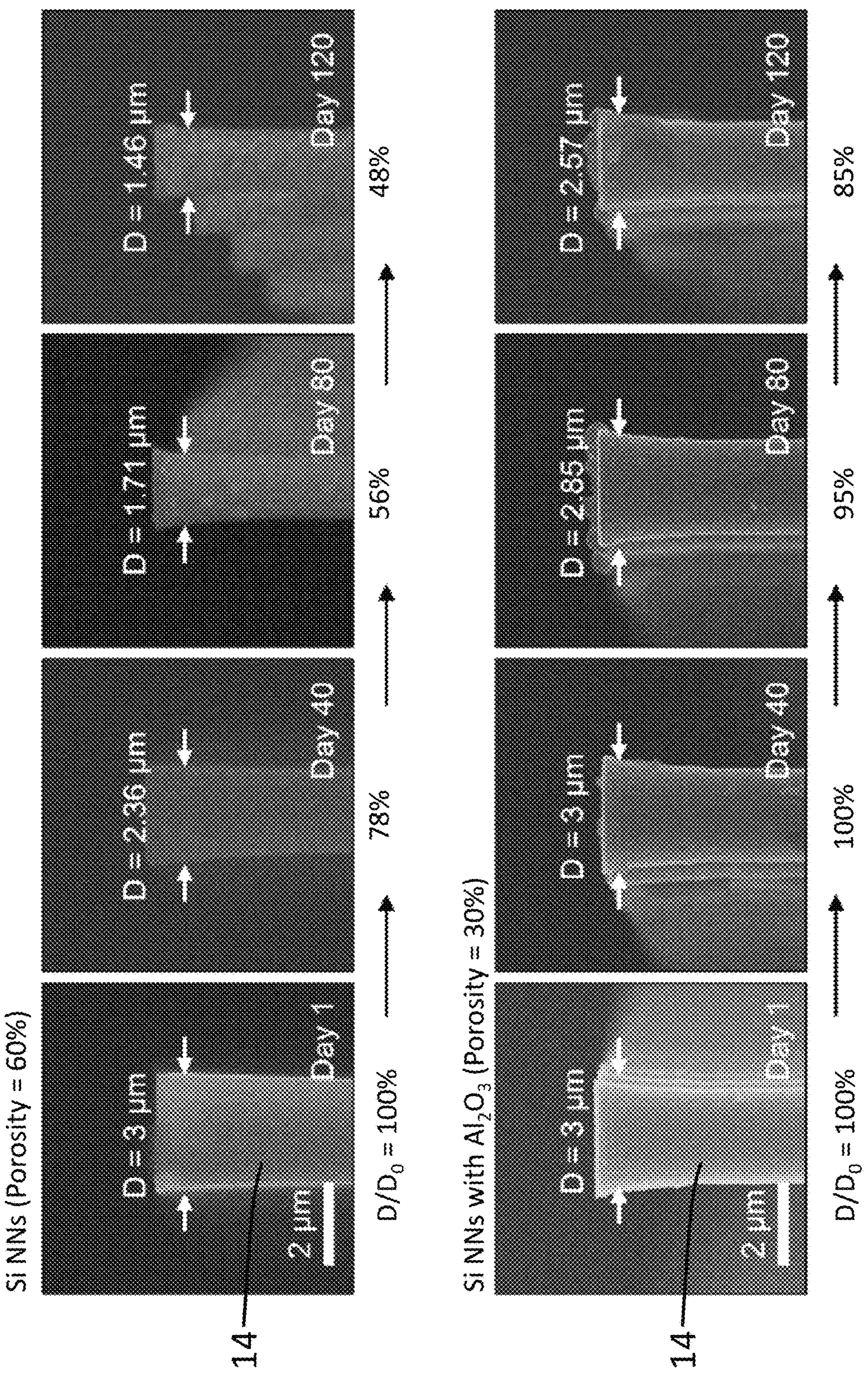
Figure 12A:
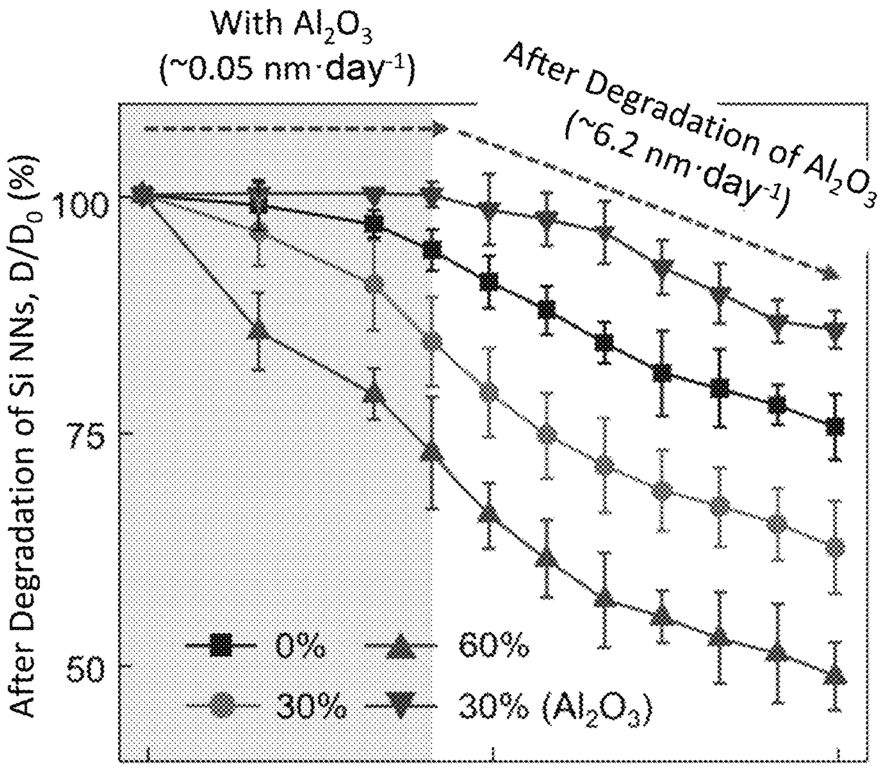
FIG. 12A is a graphical representation of dissolution of the silicon nanoneedles in a 1.4% w/v agarose gel containing a 1 ml of the simulated tear fluid at 37° C. up to four months with varied surface porosity ranging from 0 to 60% and with the presence of a 3 nm-thick pinhole-free $Al_2O_3$ layer, with all data represented as mean±standard deviation with n=5 for each group.

The degradation rate of the silicon nanoneedles 14 is adjustable to enable the controlled release of therapeutic ocular drugs within a prescribed time period. FIG. 4B presents the gradual reduction of the silicon nanoneedles 14 in diameter (D/Do) for two months while being embedded in a 1.4% w/v agarose gel containing a 1 ml of the simulated tear fluid at 37° C. The simulated tear fluid was refreshed in every day to maintain the contents. For comparison, the surface porosity of the silicon nanoneedles 14 was varied from 0% (blue line) to 30% (red line) and to 60% (green line) by which the degradation of the silicon nanoneedles was linearly accelerated from about 3.5 to about 9.4 and to about 16.6 $nm \cdot day^{-1}$, respectively. In addition, the degradation rate of the silicon nanoneedles 14 substantially decreased down to about 0.05 $nm \cdot day^{-1}$ (purple line) through the conformal passivation of a thin (i.e., about 3 nm-thick) pinhole-free layer, such as aluminum oxide ($Al_2O_3$), across the surface (i.e., porosity=30%) using an atomic layer deposition (ALD). For instance, the $Al_2O_3$-passivated silicon nanoneedles exhibited at least five orders of magnitude prolonged degradation in tear fluid as compared to typical biodegradable composites, such as PLGA and MeHA (i.e., 24-120 $\mu m \cdot day^{-1}$), that have been used for ocular drug delivery. The corresponding SEM images of the silicon nanoneedles 14 while being degraded at a prescribed time interval are shown in FIG. 11. Following the complete degradation of the $Al_2O_3$ passivation layer in approximately 50 days, the degradation rate of the silicon nanoneedles 14 was gradually returned to normal (e.g., about 3.9-7.8 $nm \cdot day^{-1}$), as shown in FIG. 12A.

Figure 4C:
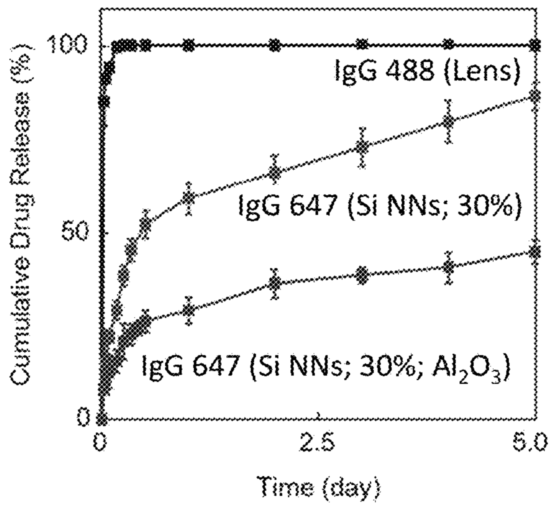
Figure 12B:
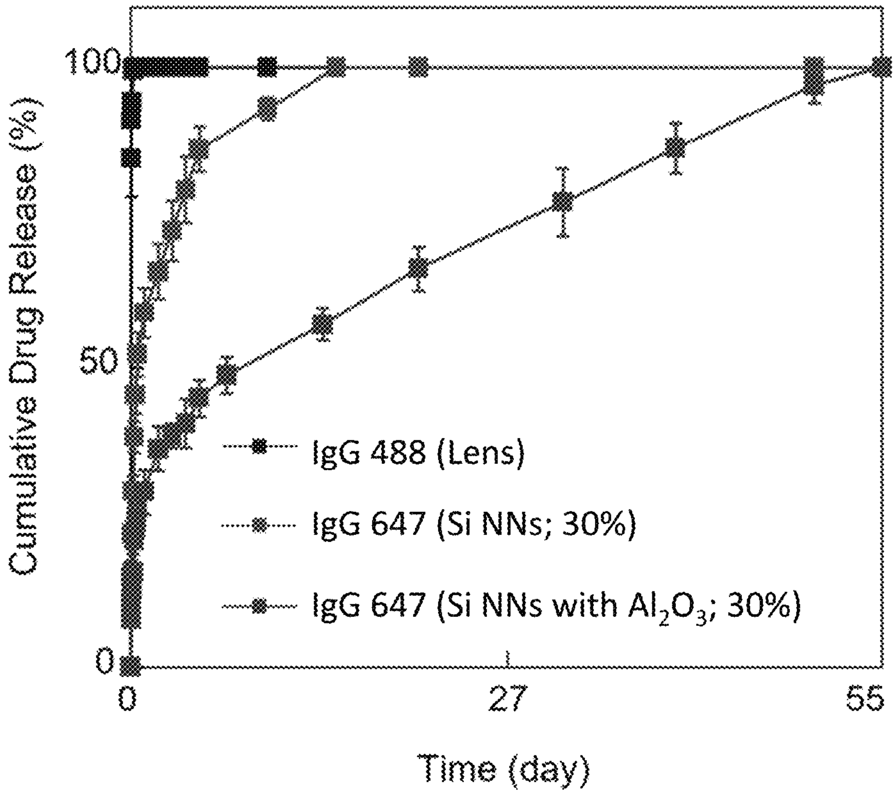
FIG. 12B is a graphical representation of cumulative release of IgG 488 and 647 for 55 days immersed in a 1 ml of the simulated tear fluid at 37° C., each of which was physically and covalently loaded in the tear-soluble contact lens (blue line) and on the surface of the silicon nanoneedles (i.e., porosity=30%) with (red line) and without (purple line) the presence of the $Al_2O_3$ passivation layer, with all data represented as mean±standard deviation with n=3 for each group.

FIG. 4C presents a release profile of the IgG 488 and 647 for five days immersed in 1 ml of the simulated tear fluid at 37° C., each of which was physically and covalently loaded in the tear-soluble contact lens (blue line) and along the surface of the silicon nanoneedles (i.e., porosity=30%) without (red line) and with (purple line) the presence of the $Al_2O_3$ passivation layer. The corresponding results displaying the complete release of the IgG 488 and 647 up to 55 days are shown in FIG. 12B. These results clearly display a biphasic release profile in which greater than 85% of the IgG 488 was quickly released from the tear-soluble contact lens 12 within a minute (i.e., burst release) followed by the prolonged release of the IgG 647 from the silicon nanoneedles 14 (i.e., long-term sustained release). The mean dissolution time (MDT), or drug retaining ability, of T50% and T80% increased from 11 to 194 hours and from 96 to 814 hours with the presence of the $Al_2O_3$ passivation layer, respectively. In turn, the $Al_2O_3$-passivated silicon nanoneedles 14 exhibited substantially prolonged MDT in tear fluid as compared to typical biodegradable composites, such as PLGA and MeHA (e.g., T50%=35-48 hours and T80%=75-120 hours), that have been used for ocular drug delivery.

Figure 4D:
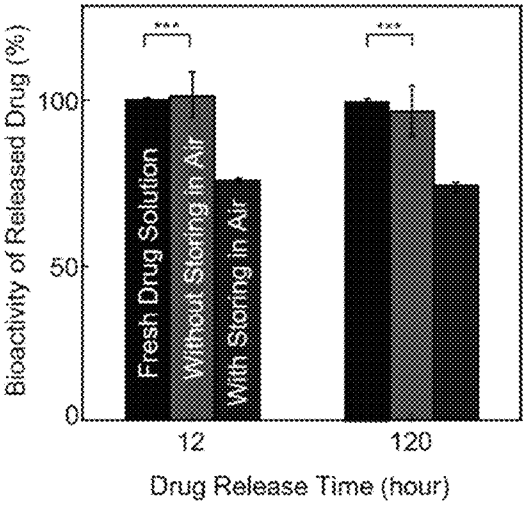

FIG. 4D presents results of an enzyme-linked immunosorbent assay (ELISA) performed to quantify the bioactivity of Bev at 12 and 120 hours of release from the silicon nanoneedles 14 (red bars) as compared to a new vial of fresh drug solution (i.e., Bev) as a control (black bars). The bioactivity of Bev was maintained over 99% for a period of 120 hours without significant difference comparing to the control with *p<0.001 (n=3 for each group). The results (blue bars) also indicate that nearly 25% of reduction in the bioactivity occurred after three days of storing in air at 4° C. due to the oxidation of the protein (i.e., Bev), suggesting that the drug loading process (e.g., step 70 of FIG. 1B) preferably occurs right before the implementation of the silicon nanoneedles 14** into the eye.

To evaluate the therapeutic efficacy of ocular drug delivery device 10 with the silicon nanoneedles 14, an investigation was conducted in an in vivo rabbit CNV model. CNV, or the invasion of new blood vessels into the avascular cornea, accounts for vision loss in 1.4 million people annually in the United States and is a potential consequence of various disorders such as dry eye syndrome, contact lens use, corneal infections, surgery, trauma, and limbal stem cell deficiency (LSCD). Vascular ingrowth into the cornea is also a major risk factor for rejection after corneal transplantation, and therefore the treatment of CNV must be considered for visually impactful CNV or before corneal transplant. The current conventional therapy for CNV involves the use of laser photocoagulation surgery, but its efficacy remains limited due to the protective barriers of the corneal surface, side effects, and rapid nasolacrimal drainage. To address this critical need, the utility of the silicon nanoneedles 14 was demonstrated in treating CNV through the minimally invasive, painless, and long-term sustained delivery of an ocular drug (i.e., Bev) for improved therapeutic efficacy with reduced side effects beyond current gold standard therapy. A total of 24 New Zealand white rabbits (three to four months old; 2.2-3.1 kg) were used in this investigation including both left and right eyes due to the similarities of the rabbit eye to the human eye. The animal procedures were as follows.

First, a 7-0 silk suture was threaded through the peripheral cornea at approximately 1.5 mm away from the limbus of the rabbit eye. CNV was well developed at day 28 post suture placement. The suture was then removed. CNV was stabilized at day seven post suture removal. Next, the rabbit eye was treated with the silicon nanoneedles 14 by inserting the tear-soluble contact lens 12 with gentle pressure using a cotton swab. Thereafter the tear-soluble contact lens 12 was dissolved in tear fluid within less than a minute. A few drops of artificial tear solution were applied to wash the rabbit eye. Finally, the rabbit eye was monitored for 28 days using color and red-free photography as well as a custom-built optical coherence tomography (OCT). For comparison, both short (i.e., 10 μm) and long (i.e., 60 μm) silicon nanoneedles were tested after covalently loaded with a total about 1.5 μg and about 14 μg of Bev, respectively. The results were also compared with control groups including (1) the silicon nanoneedles without Bev and (2) the untreated rabbit eye.

Figure 5A:
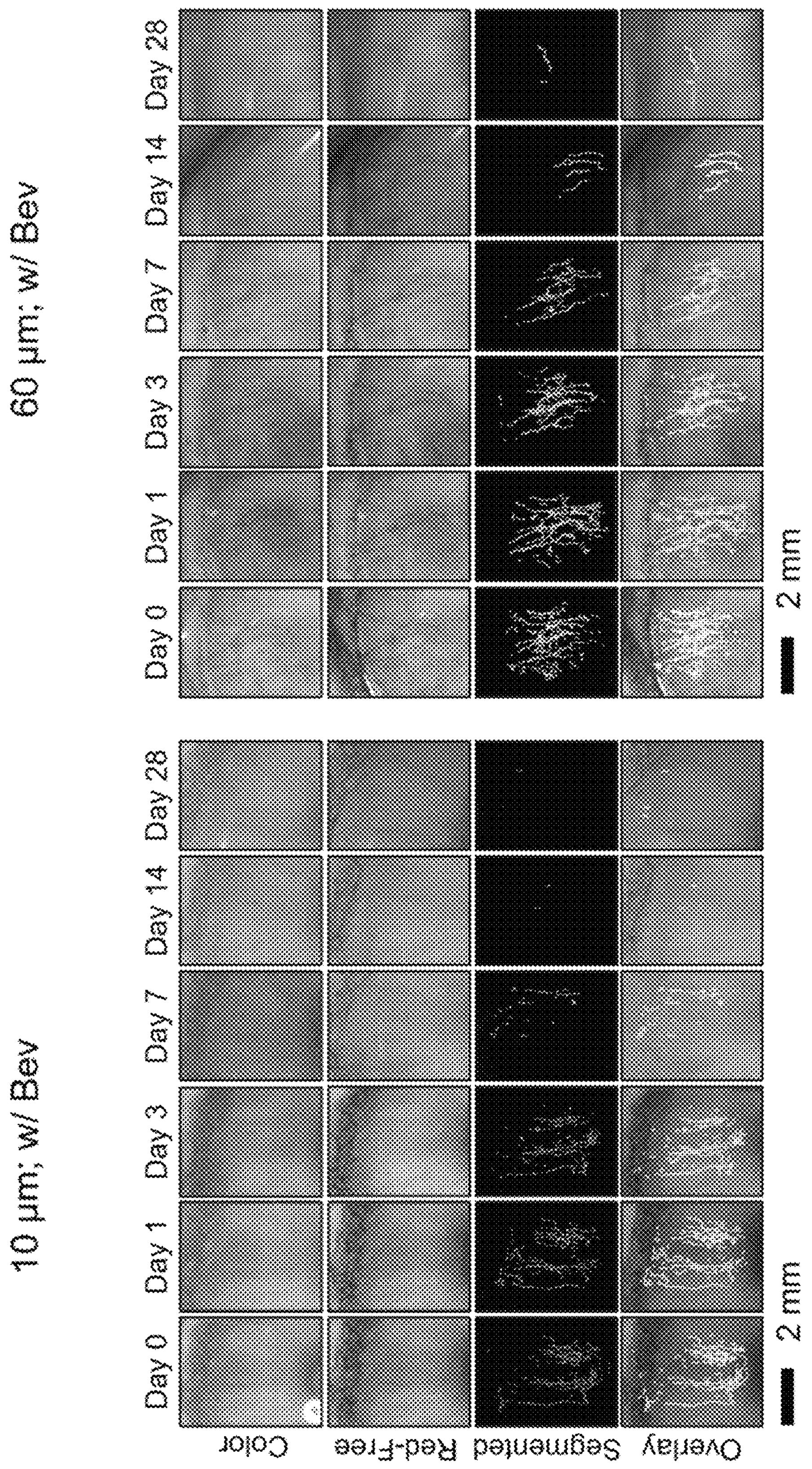
FIGS. 5A through 5C represent in vivo evaluation in a rabbit CNV model.
Figure 5B:
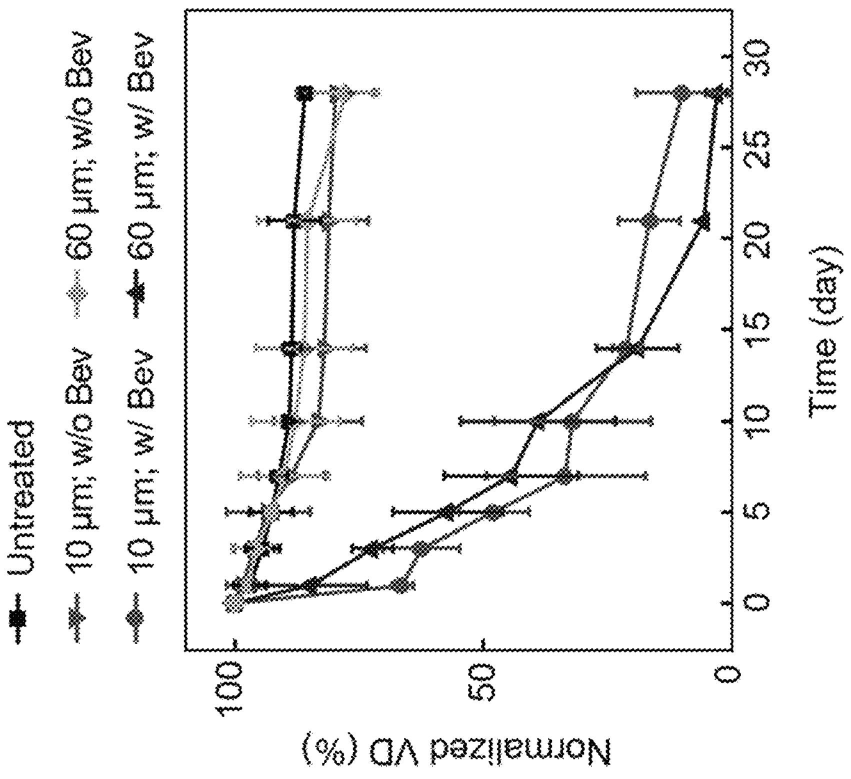

FIG. 5A shows a time series of the representative color, red-free, segmented, and overlay images of CNV at day 0 (i.e., pre-therapy) and days 1, 3, 7, 14, and 28 (i.e., on-therapy) using the 10 μm-long (left panel) and 60 μm-long (right panel) silicon nanoneedles with a fixed base diameter of 900 nm. Both groups of the silicon nanoneedles 14 showed significant effect on treating CNV without noticeable difference between the groups. Rapid reduction in CNV occurred from day 1 to 7, followed by sustained, persistent, and continued reduction up to day 28. Nearly complete removal of CNV appeared no later than day 28. In contrast, no reduction in CNV occurred in the control groups throughout the entire period. FIG. 5B summarizes the results of vessel density (VD) analysis to quantify the dynamic change of CNV from day 0 to 28. The results show that the normalized VD reduced to nearly half (i.e., 47.8±6.9% for the 10 μm-long silicon nanoneedles with Bev; and 57.2±11.1% for the 60 μm-long silicon nanoneedles with Bev) at day 5, followed by sustained, persistent, and continued reduction up to day 28 (i.e., 9.8±2.5% for 10 μm-long silicon nanoneedles with Bev; and 2.9±2.0% for 60 μm-long silicon nanoneedles with Bev). In the control groups, the normalized VD remained relatively unchanged over time (i.e., 79.7±7.7% for the 10 μm-long silicon nanoneedles without Bev; 77.8±6.6% for the 60 μm-long silicon nanoneedles without Bev; and 85.8±0.9% for the untreated group).

Figure 5C:
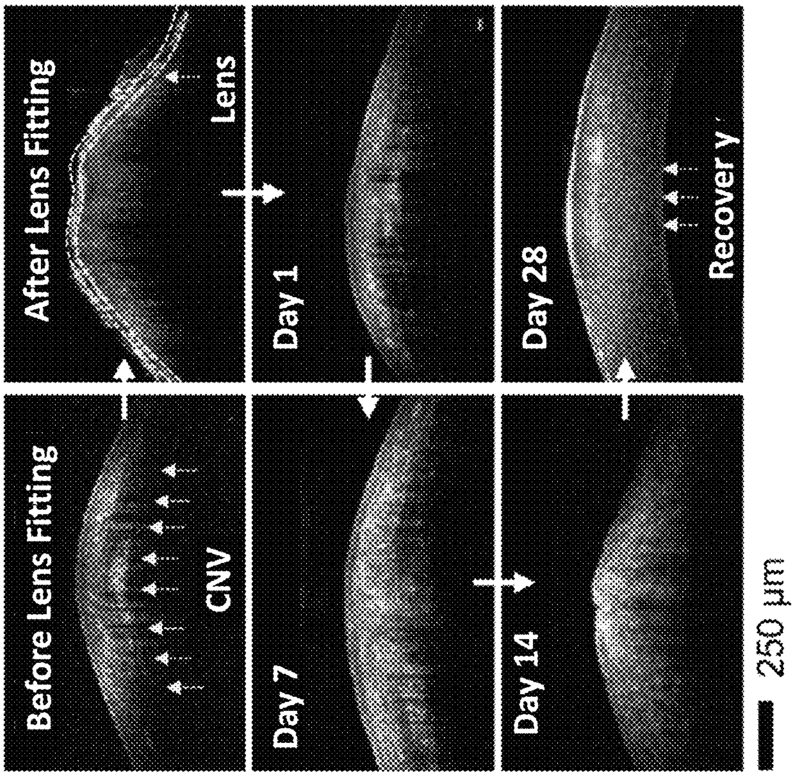

FIG. 5C provides a time series of the cross-sectional OCT images of the rabbit eye under therapy using the 60 μm-long silicon nanoneedles 14 at day 0 (i.e., right before and after the lens fitting) and days 1, 7, 14, and 28 (i.e., on-therapy). At day 0, the location of CNV (i.e., longitudinal shadows) and the tear-soluble contact lens 12 were clearly visible in the OCT images as annotated with yellow dotted arrows and lines, respectively. The silicon nanoneedles 14 were invisible in the OCT images due to the nanoscale size (i.e., 900 nm in base diameter). As consistent with the previous observations, the rapid reduction of CNV occurred from day 1 to 7, followed by sustained, persistent, and continued reduction up to day 28. The OCT image at day 28 displays the normal structure of the cornea without any evidence of corneal damage, such as hemorrhage and corneal opacification, to confirm the recovery. Pain assessment in rabbits were made using the interpretation of facial expression or grimace scale. In close daily monitoring of the rabbits, no sign of discomfort was observed, including any change of orbital tightening, cheek flattening, nose shape, whisker position, and ear position, according to the established grimace scale. The ears were roughly perpendicular to the head, facing forward or to the side, held in an upright position away from the back and sides of the body with a more open and loosely curled shape, which indicated no pain. In addition, body weight assessment in rabbits were made for 28 days of therapy. No reduction in the body weight of the rabbits was observed.

Time-dependent cytotoxicity of the silicon nanoneedles to human corneal cell lines was considered to reveal any adverse response at the cellular level. FIG. 6A presents the in vitro cell viability assay of human corneal epithelial cells (HCEpiCs) that were seeded with (red bars) and without (black bars) the 60 μm-long silicon nanoneedles for three days using an MTT (3-(4,5-dimethylthiazol-2-yl)-2,5-diphenyltetrazolium bromide) assay kit. At the beginning of the cell culture process, the tear-soluble contact lens was quickly dissolved in the culture medium at 37° C. The cell viability remained over 99% throughout the assay period without significant difference between the groups (n=5 for each group) with ***p<0.001. In turn, both the silicon nanoneedles and the tear-soluble contact lens were determined to pose little risk for the development of corneal inflammation.

Figure 6B:
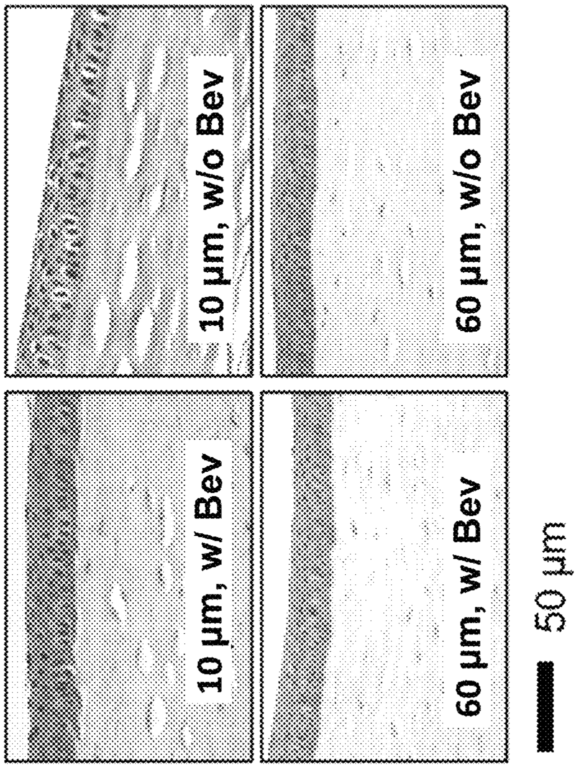
FIGS. 6A through 6F represent data obtained from biocompatibility and biosafety investigations.
Figure 6A:
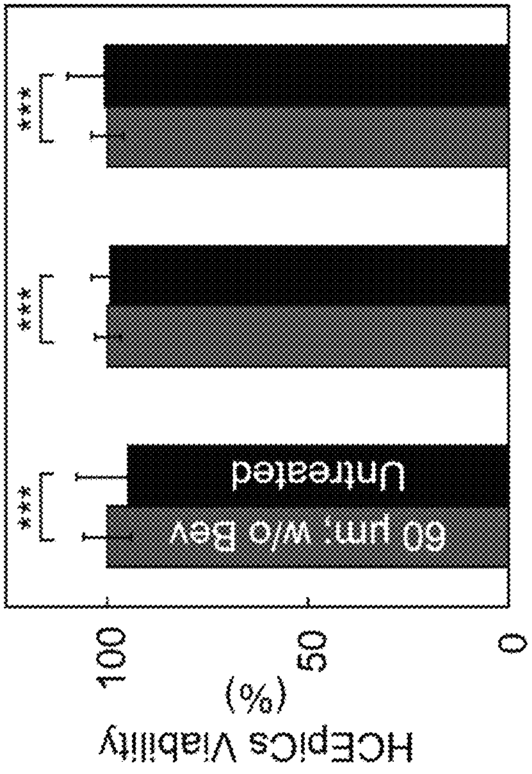

FIG. 6B shows the cross-sectional histological view of the rabbit cornea that was stained with hematoxylin-eosin (H&E) at day 28 on-therapy using the 10 μm-long (top panel) and 60 μm-long (bottom panel) silicon nanoneedles with (left panel) and without (right panel) the presence of Bev. The corneal stroma remained normal without displaying any disorganization of corneal fibrils and collagen for all the groups. In addition, there was no significant difference in the corneal epithelium thickness among the groups (n=3 for each group) with *p<0.001 (FIG. 6**C). In turn, the ocular medication using the silicon nanoneedles was determined to pose little risk for the development of corneal toxicity or other adverse reactions.

Figure 6D:
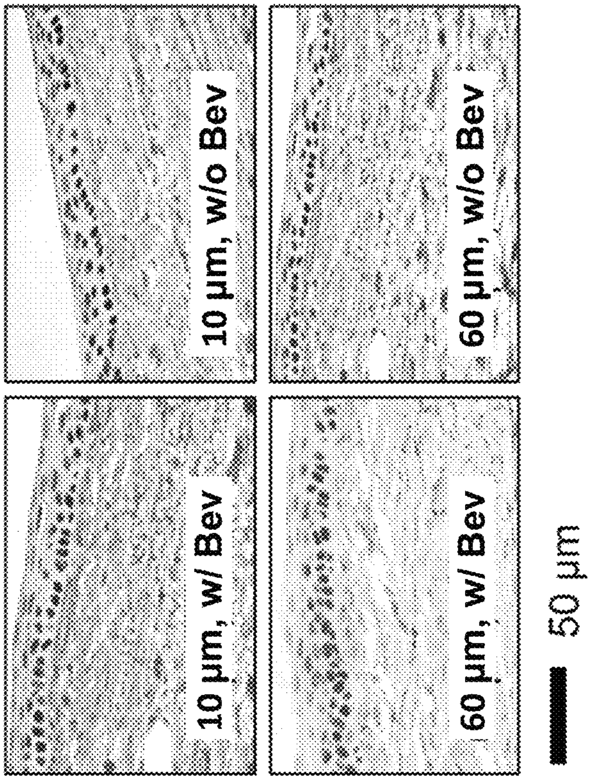
Figure 6C:
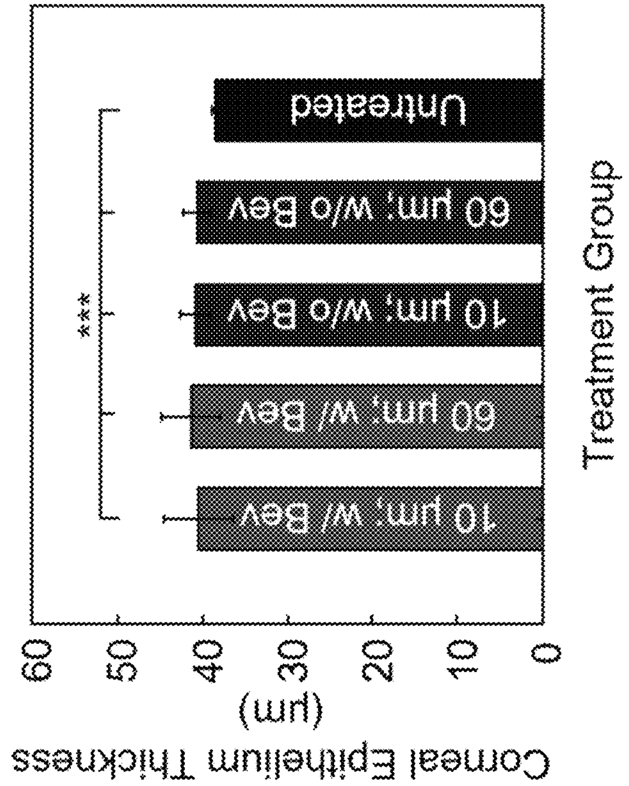
Figure 6E:
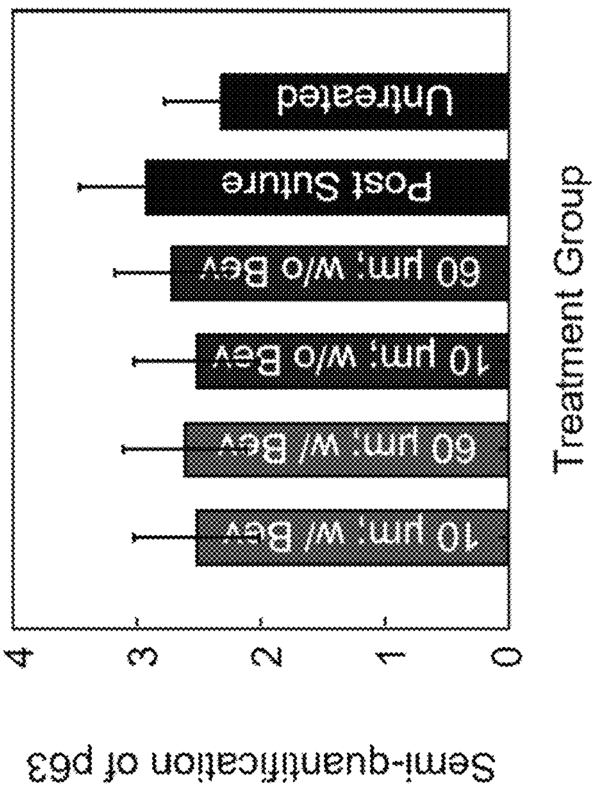
Figure 6F:
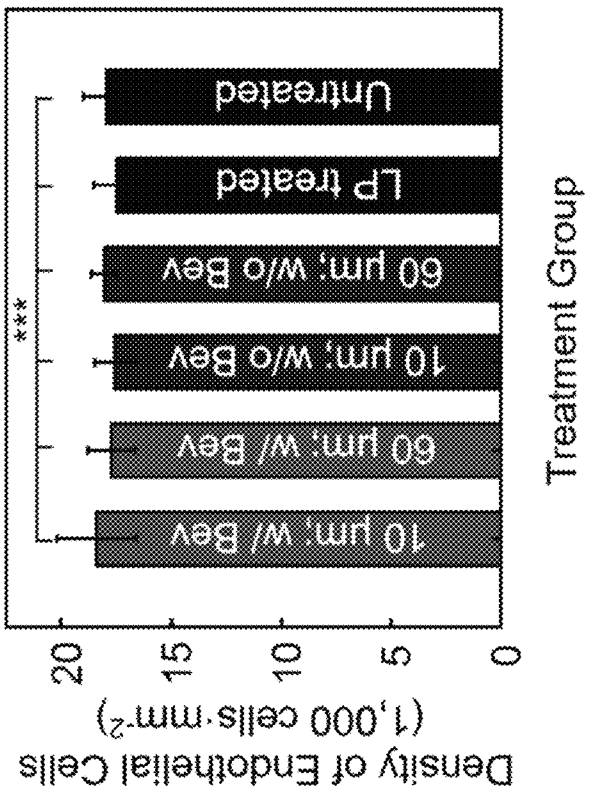

FIG. 6D shows the representative immunohistochemistry (IHC) results of the rabbit limbus that was stained with a p63 cell marker at day 28 on-therapy using the 10 μm-long (top panel) and 60 μm-long (bottom panel) silicon nanoneedles with (left panel) and without (right panel) the presence of Bev. The results show that the corneal limbus remained normal. The p63 expression remained nearly the same between the groups (n=3 for each group) without statistical significance (FIG. 6E). The density of corneal endothelial cells remained also the same between the groups (n=3 for each group) with *p<0.001 (FIG. 6**F). No sign of change in the morphology of the corneal endothelial cells appeared in H&E images. Taken together, the ocular medication using the silicon nanoneedles was determined to pose minimal toxic impacts on the corneal endothelial cells and limbal stem cell function.

For comparison, the current conventional therapy, laser photocoagulation surgery, was also implemented in treating CNV using a continuous-wave (CW) laser at 532 nm with pulse duration=0.1 sec; power=450 mW; and width=75 μm48. Numerous photocoagulation spots were noted in the cornea immediately (i.e., less than one minute) after the laser photocoagulation surgery. Circular scars were also noted in the stroma and destructure of corneal tissue along with polymorphonuclear leukocytes, inflammatory debris, and neovascularization fill clefted between the stromal lamellae. Significant reduction in the number of the limbal stem cells appeared at day 30 post-surgery. 64.7% of the CNV recovered at day 7 post-surgery while 21.4% of the CNV persisted until day 30 post-surgery. In turn, the laser photocoagulation surgery resulted in a less complete resolution of CNV as compared to the treatment using ocular drug delivery devices 10 with the silicon nanoneedles 14, while also causing damage to the surrounding corneal layers.

The investigations leading to aspects of the present invention indicated that the ocular drug delivery device 10 provides for a minimally invasive, painless, and effective method of ocular drug delivery. The prolonged degradation of the silicon nanoneedles 14 provides for longer term sustained release of therapeutic ocular drugs as compared to conventional bioresorbable microneedles. In parallel, the tear-soluble contact lens 12 serves as a temporary holder for the silicon nanoneedles 14 during lens fitting and then undergo rapid dissolution in tear fluid. The complete removal of the tear-soluble contact lens 12 helps to promote user comfort without visual disturbance. In vivo evaluations of the silicon nanoneedles 14 in a rabbit model support the therapeutic efficacy in treating a chronic ocular disease, such as CNV, with reduced side effects beyond the current conventional therapy. Therefore, the ocular drug delivery device 10 is potentially usable for clinical practice and generalizable in treating many chronic ocular diseases or injuries including glaucoma, cataract, dry eye, and graft rejection.

The silicon nanoneedles 14 may in some configurations provide any one or more of the following features: (I) sufficient mechanical stiffness (e.g., E equal to or greater than 112.4 GPa) with sharpened tips for minimally invasive penetration through the corneal barriers while causing minimal to no corneal stromal haze; (ii) at least 80-fold smaller size in base diameter as compared to typical microneedles for painless injection; (iii) at least five orders of magnitude prolonged degradation in the presence of tear fluid as compared to typical biodegradable composites (e.g., PLGA, MeHA) for long-term sustained drug delivery; (iv) adjustable surface porosity at the nanoscale for precise drug dosage control; and (v) covalently conjugated therapeutic ocular drug molecules along the surface with a strong binding affinity for leakage-free drug loading. In parallel, the tear-soluble contact lens may provide the following features: (I) sufficient mechanical stiffness (e.g., E=4 GPa) for easy lens handling and fitting; (ii) biocompatibility with the eye using a medical-grade water-soluble polymer such as poly (vinyl alcohol) (PVA) for minimal side effects; (iii) curvature (e.g., 8.3-9.0 mm in base curve radii) configured to fit a variety of corneal shapes for seamless fitting onto the eye; (iv) rapid dissolution and complete wash away with tear fluid for user comfort without visual disturbance; and (v) drug reservoir to enable an initial burst release of anti-inflammatory or other ocular drugs for enhanced therapeutic efficacy.

While the invention has been described in terms of specific or particular embodiments, it should be apparent that alternatives could be adopted by one skilled in the art. For example, the ocular drug delivery device and its components could differ in appearance and construction from the embodiments described herein and shown in the figures, functions of certain components of the ocular drug delivery device could be performed by components of different construction but capable of a similar (though not necessarily equivalent) function, process parameters such as temperatures and durations could be modified, and appropriate materials could be substituted for those noted. Accordingly, it should be understood that the invention is not necessarily limited to any embodiment described herein. It should also be understood that the phraseology and terminology employed above are for the purpose of describing the disclosed embodiment and investigations, and do not necessarily serve as limitations to the scope of the invention.

The invention claimed is:

1. An ocular drug delivery device comprising:

a contact lens having a curvature configured to fit a cornea of an eye, the contact lens being tear-soluble and dissolving when in contact with the cornea;

an array of nanoneedles attached to and protruding from a surface of the contact lens; and a therapeutic drug cargo loaded onto individual nanoneedles of the array of nanoneedles.

2. The ocular drug delivery device of claim 1, wherein the individual nanoneedles are configured to gradually degrade over a longer period of time than the contact lens when in contact with the cornea of the eye causing release of the therapeutic drug cargo after the contact lens is dissolved.

3. The ocular drug delivery device of claim 2, wherein the individual nanoneedles are made of silicon and degrade via gradual hydrolysis due to fluids in the cornea or tear fluids thereon.

4. The ocular drug delivery device of claim 1, wherein the therapeutic drug cargo is covalently and physically bonded to surfaces of the individual nanoneedles.

5. The ocular drug delivery device of claim 1, wherein the individual nanoneedles are configured to degrade and release the therapeutic drug cargo in a manner that reaches a sustained predetermined dose at or above a minimum inhibitory concentration of the therapeutic drug cargo.

6. The ocular drug delivery device of claim 1, wherein the contact lens is formed of a water-soluble polymer.

7. The ocular drug delivery device of claim 6, wherein the contact lens includes a hole at the pupil area thereof.

8. The ocular drug delivery device of claim 6, further comprising a secondary therapeutic drug cargo loaded onto the contact lens, wherein dissolving the contact lens causes release of the secondary therapeutic drug cargo faster than release of the therapeutic drug cargo loaded onto the nanoneedles.

9. The ocular drug delivery device of claim 6, wherein the contact lens comprises polymerized poly (vinyl alcohol) film and is configured to dissolve in one minute or less.

10. The ocular drug delivery device of claim 1, wherein the individual nanoneedles have minimum base diameters of 0.9 μm, and minimum lengths of 1 μm.

11. The ocular drug delivery device of claim 10, wherein the individual nanoneedles have minimum tip diameters of 50 to 900 nm, base diameters of 0.9 to 5 μm, and lengths of 1 to 100 μm.

12. The ocular drug delivery device of claim 1, wherein the individual nanoneedles have an average porosity of about 0 to 80 percent.

13. A method of fabricating the ocular drug delivery device of claim 1, the method comprising:

forming an array of vertically ordered, nanoscopic, porous pillars on a substrate, individual pillars of the array of vertically-ordered nanoscopic porous pillars having distal ends extending away from the substrate and proximal ends adjacent the substrate, the individual pillars each having an undercut formed therein at the proximal end thereof that has a minimum diameter of the individual pillar;

forming a flexible film parallel to the substrate with an air gap therebetween, wherein distal ends of the individual pillars are embedded in the flexible film;

peeling the flexible film away from the substrate such that proximal ends of the individual pillars break away from the substrate at the undercuts thereof and the distal ends of the individual pillars remain embedded in the flexible film, the individual pillars remaining in the flexible film defining the array of nanoneedles;

deforming the flexible film into the contact lens; and loading the individual nanoneedles with the therapeutic drug cargo.

14. The method of claim 13, wherein the flexible film is formed by:

spin casting the substrate having the individual pillars thereon with a pre-cured solution while allowing the air gap to form therebetween due to surface tension; and thermally annealing the spin-cast, pre-cured solution to form the flexible film.

15. The method of claim 13, further comprising forming a hole in a pupil area of the contact lens.

16. The method of claim 13, further comprising loading the contact lens with a secondary therapeutic drug cargo.

17. A method of releasing a therapeutic drug cargo to an eye, the method comprising:

providing an ocular drug delivery device that includes an array of nanoneedles attached to a surface of a contact lens;

applying the ocular drug delivery device to an eye such that the surface of the contact lens contacts the cornea of the eye and individual nanoneedles of the array of nanoneedles are inserted into the cornea; and dissolving the contact lens while leaving the individual nanoneedles inserted in the cornea;

wherein the individual nanoneedles degrade in the cornea over time causing release of a therapeutic drug cargo loaded onto the individual nanoneedles.

18. The method of claim 17, wherein the therapeutic drug cargo is covalently and physically bonded to surfaces of the individual nanoneedles.

19. The method of claim 17, wherein the ocular drug delivery device is applied to the eye such that a hole in a pupil area of the contact lens is located over a pupil of the eye.

20. The method of claim 17, wherein dissolving the contact lens releases a secondary therapeutic drug cargo loaded onto the contact lens.

* * * * *